(12) United States Patent
Rand et al.

(10) Patent No.: US 7,618,773 B2
(45) Date of Patent: Nov. 17, 2009

(54) HEADLOOP DNA AMPLIFICATION

(75) Inventors: Keith Rand, Frenchs Forest (AU); Peter Laurence Molloy, Chatswood (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 10/505,779

(22) PCT Filed: Feb. 26, 2003

(86) PCT No.: PCT/AU03/00244

§ 371 (c)(1), (2), (4) Date: Jun. 6, 2005

(87) PCT Pub. No.: WO03/072810

PCT Pub. Date: Sep. 4, 2003

(65) Prior Publication Data

US 2005/0221312 A1    Oct. 6, 2005

(30) Foreign Application Priority Data

Feb. 26, 2002    (AU)    ..... PS0768

(51) Int. Cl.
*C12Q 1/68* (2006.01)
*C12P 19/34* (2006.01)
*C07H 21/04* (2006.01)

(52) U.S. Cl. ........... 435/6; 435/91.2; 536/24.33

(58) Field of Classification Search ......... None
See application file for complete search history.

(56) References Cited

U.S. PATENT DOCUMENTS 5,565,340 A * 10/1996 Chenchik et al. ......... 435/91.2
6,326,145 B1 * 12/2001 Whitcombe et al. ......... 435/6

FOREIGN PATENT DOCUMENTS

| JP | 09-511149 | 11/1997 |
|---|---|---|
| WO | 96/23079 A2 | 8/1996 |
| WO | 99/55905 A1 | 11/1999 |
| WO | WO 99 55905 A | 11/1999 |

OTHER PUBLICATIONS

Bottema et al. Polymerase chain reaction amplification of specific alleles: A general method of detection of mutations, polymorphisms, and haplotypes. Methods in Enzymology (1993) 218: 388-402.*
Brill et al. Differentiation between spore-forming and asporogenic bacteria using a PCR and Southern hybridization based method. Journal of Microbiological Methods. (1997) 31: 29-36.*
Henke et al. Betaine improves the PCR amplification of GC-rich DNA sequences. Nucleic Acids Research. (1997) 25(19): 3957-3958.*
Wilton et al. Snapback SSCP analysis: Engineered conformation changes for the rapid typing of known mutations. Human Mutation (1998) 11: 252-258.*
Devon et al. Splinkerettes—improved vectorettes for greater efficiency in PCR walking. Nucleic Acids Research 23(9): 1644-1645 (1995).*
Potaman, V.N. Prevention of Unexpectedly Long PCR Products Primed at Short Inverted Repeats. BioTechniques 27: 1110, 1112, and 1114 (1999).*
International Search Report for PCT/AUO3/00244 dated May 21, 2003.
International Preliminary Examination Report for PCT.AUO3/00244 dated Jun. 2, 2004.
Supplemental European Search Report dated Sep. 24, 2007.
Natalia E. Broude, et al., "PCR based targeted genomic and cDNA differential display", Genetic Analysis: Biomolecular Engineering, 1999, pp. 51-63, vol. 15.
James G. Herman, et al., "Methylation-specific PCR: A novel PCR assay for methylation status of CpG islands", Proc. Natl. Acad. Sci. USA, 1996, pp. 9821-9826, vol. 93.
I. A. Nazarenko, et al., "A closed tube format for amplification and detection of DNA based on energy transfer", Nucleic Acids Research, 1997, pp. 2516-2521, vol. 25, No. 12.
Natalia E. Broude, "Stem-loop oligonucleotides: a robust tool for molecular biology and biotechnology", Trends in Biotechnology, 2002, pp. 249-256, vol. 20, No. 6.
Natalia E. Broude et al., "PCR based targeted genomic and cDNA differential display", Genetic Analysis: Biomolecular Engineering, vol. 15, pp. 51-63, 1999.
James G. Herman et al., "Methylation-specific PCR: A novel PCR assay for methylation status of CpG islands", Proc. Natl. Acad. Sci., vol. 93, pp. 9821-9826, 1996.

* cited by examiner

Primary Examiner—Kenneth R. Horlick
Assistant Examiner—Angela Bertagna
(74) *Attorney, Agent, or Firm*—Sughrue Mion, PLLC

(57) ABSTRACT

A method for the selective amplification of a target nucleic acid in a sample comprising the target nucleic acid and at least one non-target nucleic acid, the method comprising amplifying the nucleic acids by means of at least one oligonucleotide primer comprising:

a primer region that can prime and extend on the target and non-target nucleic acids; and a region that is an inverted repeat of an internal sequence of an amplicon of the at least one non-target nucleic acid but which contains at least one mismatch to the corresponding internal sequence, if present, of an amplicon of the target nucleic acid.

36 Claims, 12 Drawing Sheets

Figure 1. Principle of Headloop Suppression PCR
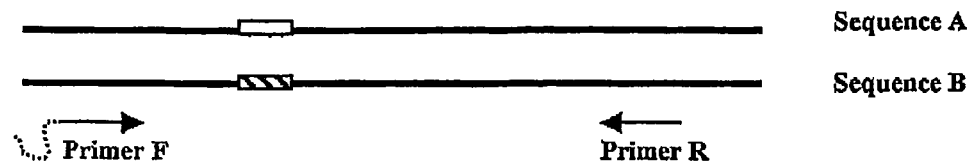
*First (Bottom) Strand Synthesis*
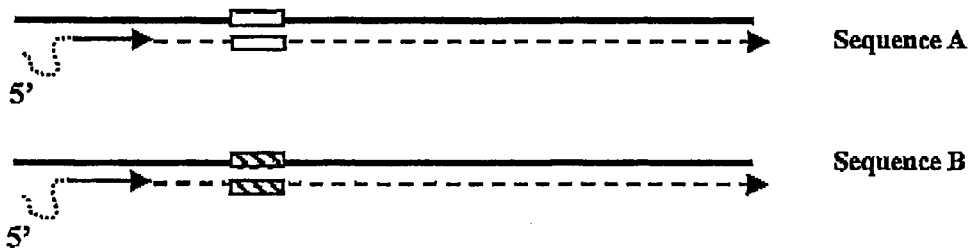
*Second (Top) Strand Synthesis*
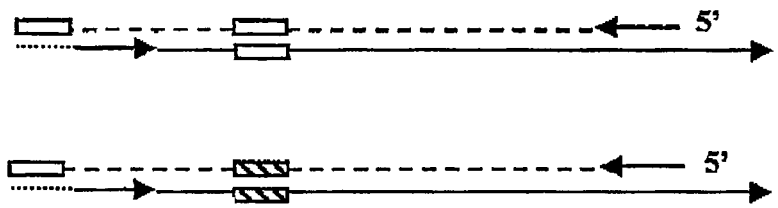
*Headloop Extension of Top Strand*
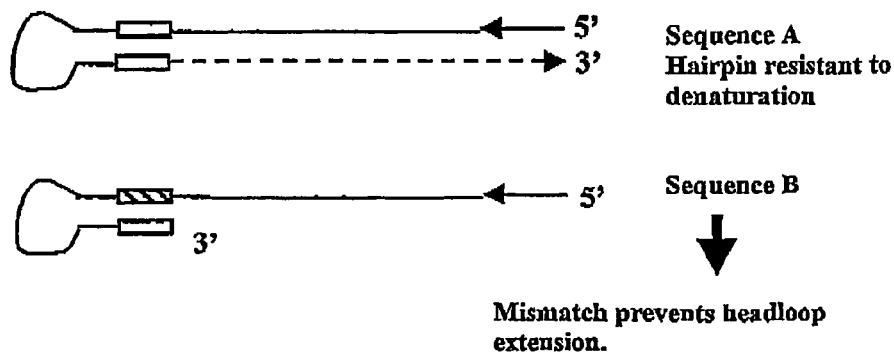
Sequence A
Hairpin resistant to denaturation
Sequence B
↓
Mismatch prevents headloop extension.

Figure 3
EHL48 headloop priming on E. coli sequence
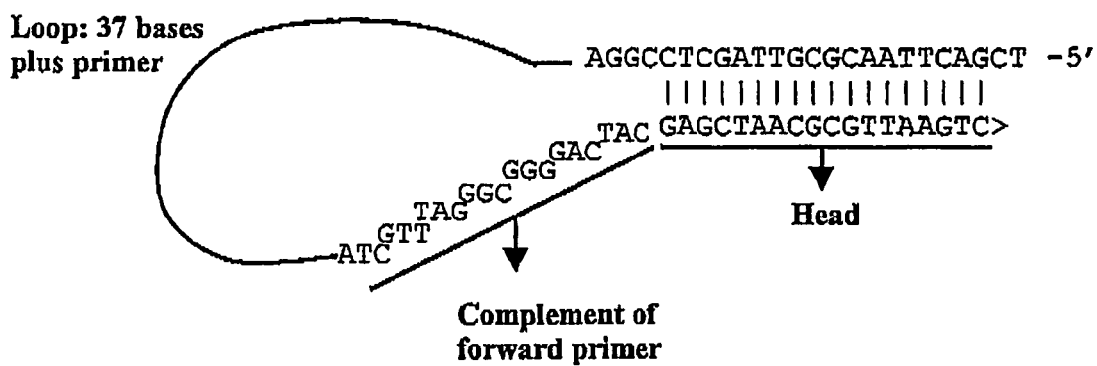
EHL48 headloop priming on S. acidophilus DNA
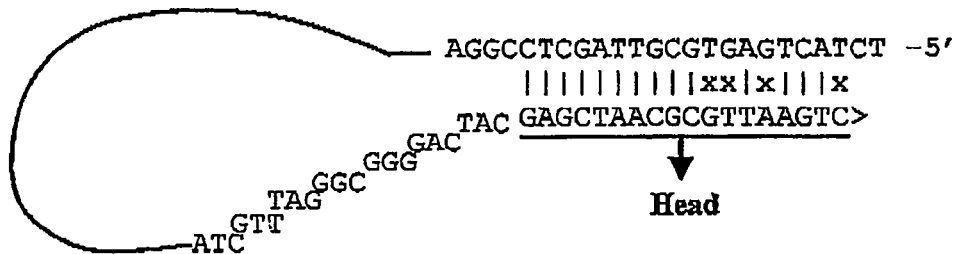

Figure 4
Panel A: 1pg E.coli : 1pg S. acidophilus
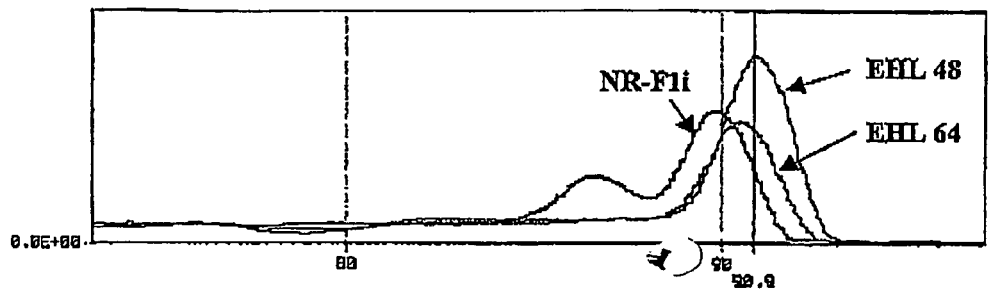
Panel B  1pg E. coli : 1pg S.thermosulfooxidans
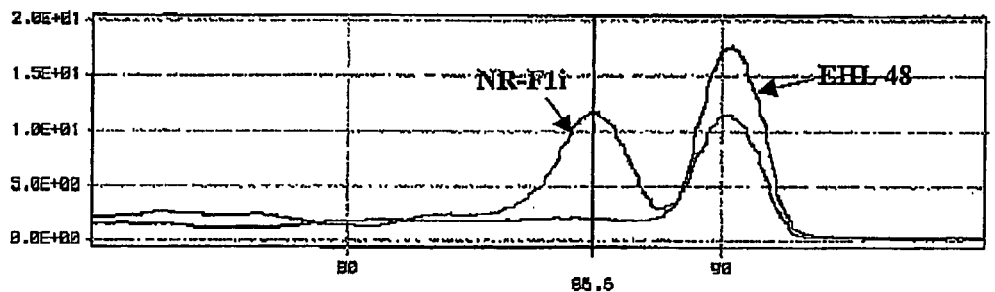
Panel C  50pg E.coli : 1pg S. thermosulfooxidans
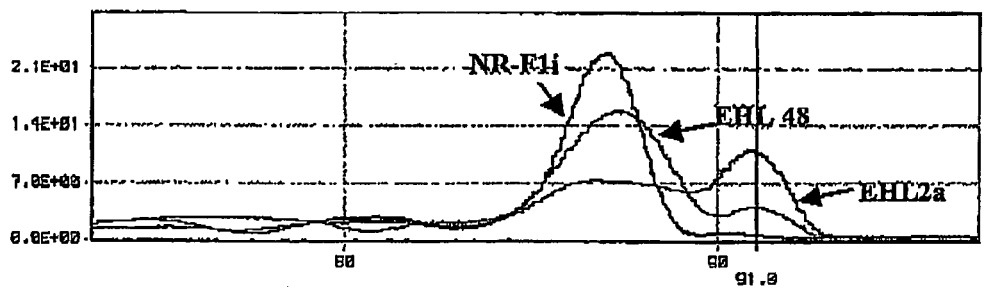
Panel D  50pg S.acidophilus : 1 pg E. coli
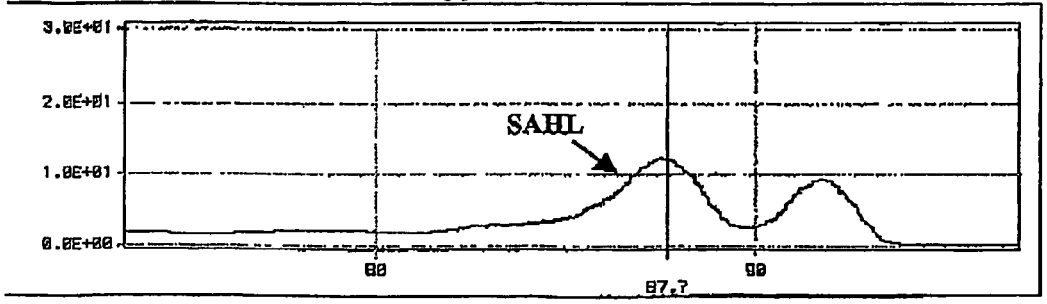

Figure 5
Panel A  *50pg S. acidophilus : 1 pg E. coli, SAHL headloop primer*
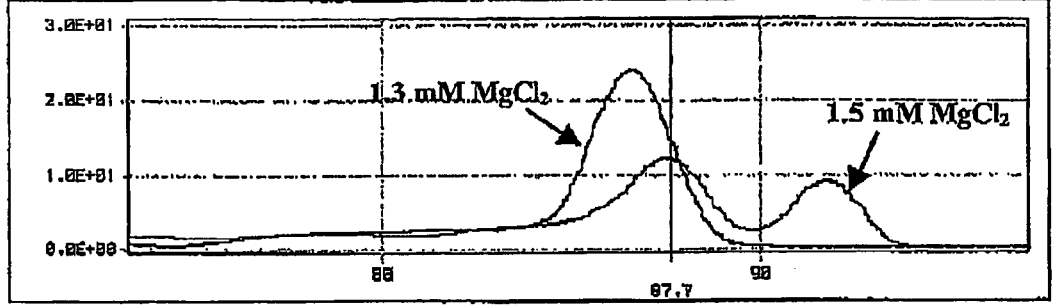
Panel B  *250pg S. acidophilus : 1 pg E. coli, SAHL headloop primer*
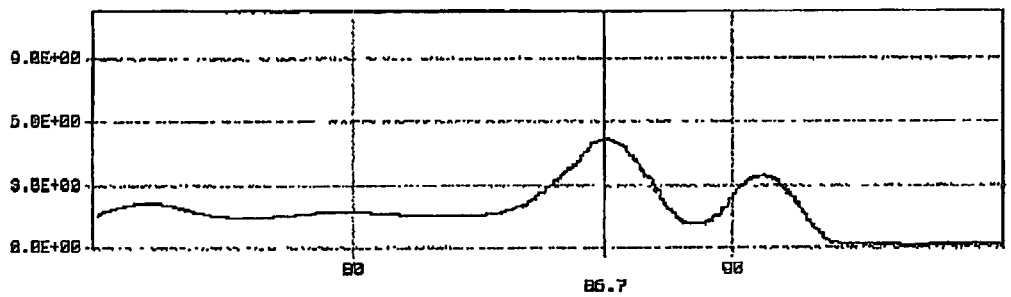
Panel C  *500pg S. acidophilus : 1 pg E. coli, SAHL headloop primer*
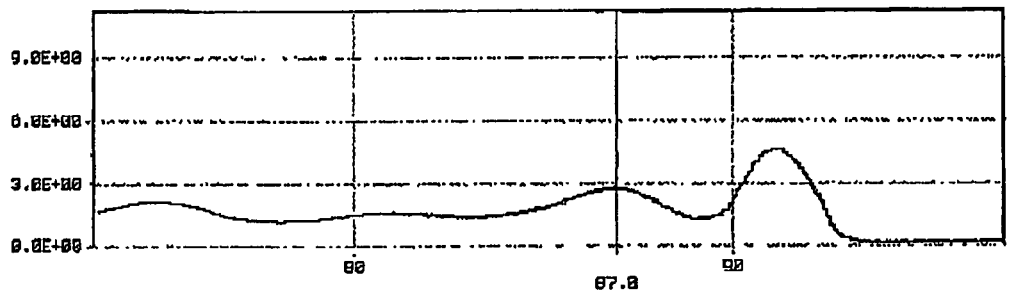
Panel D  *50pg S. acidophilus : 1 pg E. coli, SAHL headloop primer*
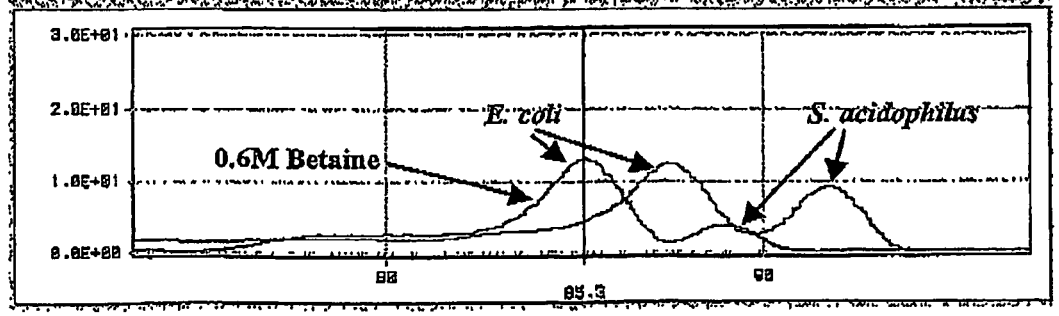

Figure 12

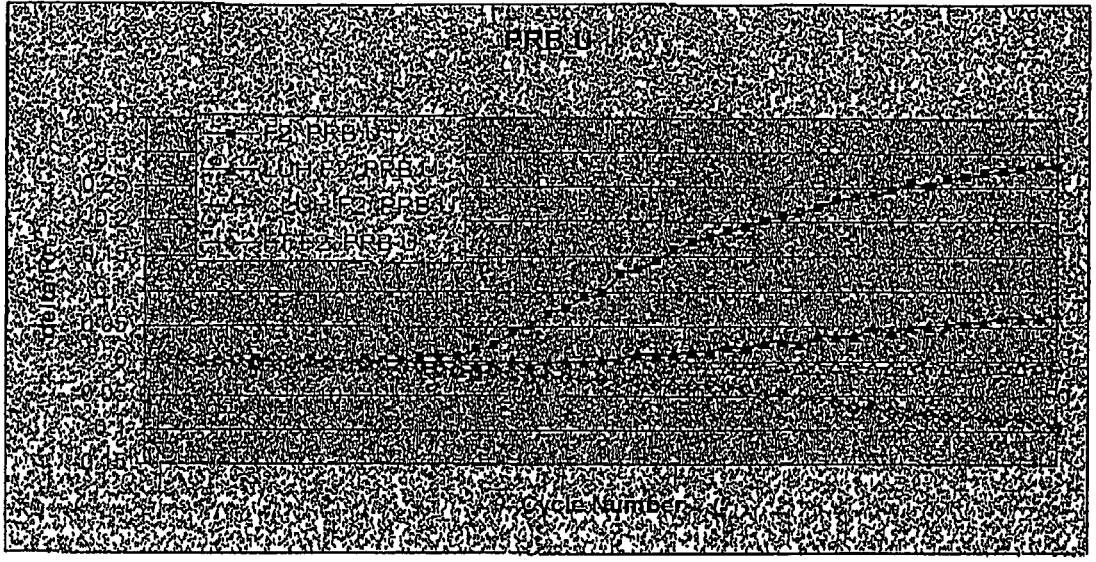

Figure 13

*GSTP1* Intragenic Region Primers

```
            -7         -6         -5                     -4         -3
     CAGCACTGGG GCGGAGCGGG GCGGGACCAC CCTTATAAGG CTCGGAGGCC
     TAGTATTGGG GCGGAGCGGG GCGGGATTAT TTTTATAAGG TTCGGAGGTC B-M
         GST F52A          GGGATTAT TTTTATAAGG TTaGGAGGT>

-2        -1 >        1  2  3         4
     GCGAGGCCTT CGCTGGAGTT TCGCCGCCGC AGTCTTCGCC ACCAGTGAGT
     GCGAGGTTTT CGTTGGAGTT TCGTCGTCGT AGTTTTCGTT ATTAGTGAGT B-M 5 6 7      8 9     10
     ACGCGCGGCC CGCGTCCCCG GGGATGGGGC TCAGAGCTCC CAGCATGGGG
     ACGCGCGGTT TGTGTTTTTG GGGATGGGGT TTAGAGTTTT TAGTATGGGG B-M
                <AAAIC CCCATCCCCA AATCTC  5-10Ni base pr TGTGTGGTT  TGTGTTTTTG                5-10Ni & 5-10 head
     TGTGTGGTT  TGTGTTTTTG  GGGATG              5-10x head <TACCCCA AATCTCAAAA ATCATACCC
                           5-10 & 5-10x base pr
```

Figure 15
Headloop primer HLINT5-10
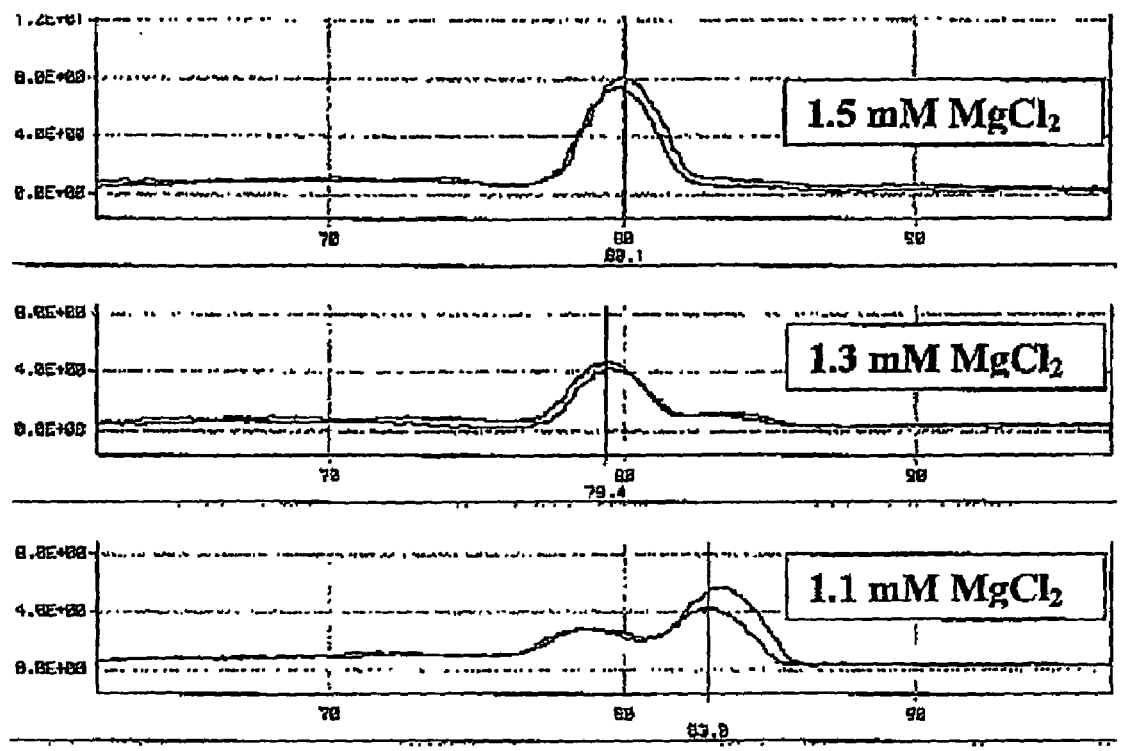
Headloop primer HLINT5-10Ni
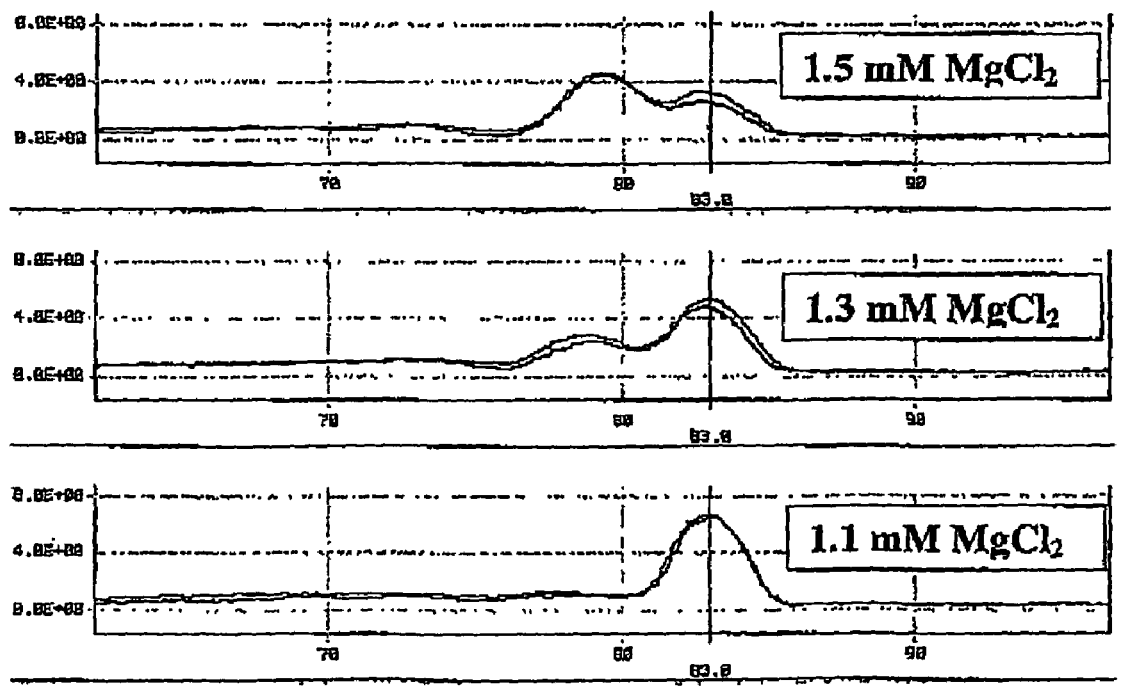

HEADLOOP DNA AMPLIFICATION

CROSS-REFERENCE TO RELATED APPLICATION

This application is a 371 of PCT/AU03/00244, filed Feb. 26, 2003; the disclosure of which is incorporated herein by reference.

FIELD OF THE INVENTION

The present invention is concerned with the selective amplification of a template molecule, especially a nucleic acid. In a particular aspect, the present invention is concerned with, but not limited to, a method for the amplification of DNA and novel primers for use in the method. The present invention also extends to specific applications of the method of the invention.

BACKGROUND TO THE INVENTION

The polymerase chain reaction (PCR) is based on repeated cycles of denaturation of double stranded DNA, followed by oligonucleotide primer annealing to the DNA template, and primer extension by a DNA polymerase (eg see Mullis et al U.S. Pat. Nos. 4,683,195, 4,683,202 and 4,800,159). The oligonucleotide primers used in PCR are designed to anneal to opposite strands of the DNA, and are positioned so that the DNA polymerase-catalysed extension product of one primer can serve as a template strand for the other primer. The PCR amplification process results in the exponential increase of discrete DNA the length of which is defined by the 5' ends of the oligonucleotide primers.

In our copending International application entitled "Nucleic acid amplification" filed on 25 Feb. 2003, the entire disclosure of which is incorporated herein by reference, we describe the of method for the selective amplification of a nucleic acid using a primer that includes a region the is an inverted repeat of a sequence in a non-target nucleic acid.

Specificity in PCR amplification of DNA is principally determined by the sequence of the primers in combination with the temperature at which the annealing step is conducted. For closely related sequences, additional approaches have been incorporated to provide selective amplification. Where a sequence difference corresponds to a restriction enzyme site, restriction enzyme digests can be used to cut an unwanted sequence and prevent its amplification. Another method of suppressing amplification is the use of oligonucleotides or PNA (peptide nucleic acid) molecules that anneal to one of the DNA strands, within the region to be amplified and/or overlapping the binding site of one of the primers, and prevent initiation or elongation of DNA synthesis. Such oligonucleotides are designed to preferentially anneal with and suppress amplification of one of two related sequences.

We describe below a novel method for selectively suppressing the amplification of one or more closely related sequences while using PCR primers that can prime and extend on both the target and suppressed sequences.

DISCLOSURE OF THE INVENTION

In a first aspect, the present invention provides a method for the selective amplification of a target nucleic acid in a sample comprising the target nucleic acid and at least one non-target nucleic acid, the method comprising amplifying the nucleic acids by means of at least one oligonucleotide primer comprising:

a primer region that can prime and extend on the target and non-target nucleic acids; and a region that is an inverted repeat of an internal sequence of an amplicon of the at least one non-target nucleic acid but which contains at least one mismatch to the corresponding internal sequence, if present, of an amplicon of the target nucleic acid.

Preferably, the inverted repeat is an extension at the 5' end of the primer.

The primer of the first aspect is also referred to as the "headloop primer".

DETAILED DESCRIPTION OF THE INVENTION

Whilst the present method may involve the use of a single primer, it is preferred that the amplification be "exponential" and so utilize a pair of primers, generally referred to as "forward" and "reverse" primers, one of which is complementary to a nucleic acid strand and the other of which is complementary to the complement of that strand. Where a pair of amplification primers is used, either one or both primers may include an inverted repeat sequence.

The amplification may be performed by any suitable amplification technique such as, for example, PCR. The PCR may be real time PCR.

The length of the primer, excluding the inverted repeat portion, may be of any length suitable for the amplification method, typically between about 15 to 35 bases.

The inverted repeat portion of the primer (alternatively referred to herein as the head) may comprise a number of nucleotides sufficient to allow priming on a matched sequence under the annealing and extension conditions of the amplification, typically in the range of about 5 to 30 bases.

The method of the present invention has particular application in the selective amplification of a target sequence from two or more closely related sequences.

Accordingly, in a second aspect, the present invention provides a method for the selective amplification of a target nucleic acid in a sample comprising the target nucleic acid and at least one closely related non-target nucleic acid, the method comprising amplifying the nucleic acids by means of at least one oligonucleotide primer comprising a primer region that can prime and extend on the target and non-target nucleic acids; and a region that is an inverted repeat of an internal sequence of an amplicon of the at least one non-target nucleic acid but which contains at least one mismatch to the corresponding internal sequence, if present, of the target nucleic acid.

In one embodiment of the present invention, the nucleic acid may be a methylated nucleic acid. Thus the method of the invention may, be used to enable selective amplification of either methylated or unmethylated DNA.

Accordingly, in a third aspect, the present invention provides a method according to the first or second aspects in which the target and non-target nucleic acids are formed by chemical modification of nucleic acid prior to amplification.

For example, the method may be applied to DNA chemically modified with sodium bisulphite in order to allow selective amplification of methylated DNA, whilst suppressing the unmethylated sequences. The methylated DNA may be sequences of a human gene, for example, GSTP1 gene. In International Patent application publication no. WO 99/55905 (the disclosure of which is incorporated in its entirety herein by cross-reference), we disclose a diagnostic or prognostic assay for a disease or condition (e.g. prostate cancer, liver cancer and breast cancer) characterised by abnormal methylation of cytosine at a site or sites within the glutathione-S-transferase (GST) Pi gene and/or its regulatory flanking sequences.

The assay described in WO 99/55905 is based on the use of methylation specific primers that are specific for methylated cytosine at a site or sites within the GSTP1 gene and/or its regulatory flanking sequence. In contrast, the method of the present invention is based on the use of primers that are capable of priming both target and non-target nucleic acid but owe their selectivity for amplification of target nucleic acid to the use of a primer including a region that is an inverted repeat of an internal sequence of an amplicon of the non-target nucleic acid. The method of the present invention thus provides an alternative to the methylation specific primer methodology described in WO/9955905.

Accordingly, in yet a fourth aspect, the present invention provides an assay for abnormal methylation of cytosine at a site or sites within the glutathione-S-transferase (GST) Pi gene and/or its regulatory flanking sequences, wherein the assay comprises exposing isolated DNA to reactants and conditions for the amplification of a target region within the GSTP1 gene and/or its regulatory flanking sequences, the target region being one or more sites at which abnormal cytosine methylation occurs, the amplification being carried out using of at least one oligonucleotide primer comprising:

a primer region that can prime and extend on the target region and a non-target region that is non-methylated, within the isolated DNA; and a region that is an inverted repeat of an internal sequence of an amplicon of the non-target region but which contains at least one mismatch to the corresponding internal sequence of the target region; and (iii) determining the presence of amplified DNA.

The target region may be a nucleic acid sequence within the region of the GSTP1 gene and/or its regulatory flanking sequences defined by (and inclusive of) CpG sites −43 to +55.

The isolated DNA of the fourth aspect of the invention may be subjected to chemical modification to convert unmethylated cytosines to uracil. The chemical modification may be achieved by bisulphite treatment.

The assay of the fourth aspect may be used as a diagnostic or prognostic assay for a disease or condition in a subject, said disease or condition characterised by abnormal methylation of cytosine. The disease or condition may be a cancer. The cancer may be, for example, prostate, liver or breast cancer.

In a particular example described below, the method of the invention is used for the selective amplification of methylated DNA present in an excess of unmethylated sequences. Following treatment with sodium bisulphite, cytosines (Cs) are converted to uracils (Us) while methyl cytosines remain unconverted. In this case, the head sequence is designed to be an inverted repeat of the downstream sequence expected to result from the bisulphite conversion of an unmethylated DNA fragment. After it has been copied, the added sequence causes self-priming on fragments derived from unmethylated DNA, leading to inhibition of the amplification of unmethylated fragments. Because the downstream sequence is chosen to contain several CpG sites (and which bisulphite conversion does not occur in the case of methylated DNA) there is insufficient complementarity to allow self-priming and thus little or no inhibition of the amplification of the methylated DNA fragments.

The method of the invention may also be used in other contexts, for instance, to distinguish allelic variants or mutations, and members of gene families. DNAs containing mutations within a short sequence region can be amplified while suppressing amplification of the wild-type sequence (eg for tumour suppressor genes).

The present invention may also be applied to the selective amplification of DNA of minor species (eg of bacteria) in an environment, by suppression of amplification of sequences of dominant species.

In a fifth aspect, the present invention includes oligonucleotide primers for template amplification, the primers including an inverse repeat of a nucleic acid sequence within the non-target amplicon but which is mismatched with the corresponding sequence of a target nucleic acid.

The invention further includes a kit, the kit including at least one oligonucleotide primer in accordance with the invention.

This invention also includes amplification methods and assays that utilize such primers, and kits for performing such assays.

Terminology

The terms "primer" and "primer region" as used in the present application, refer to an oligonucleotide which is capable of acting as a point of initiation of synthesis in the presence of nucleotide and a polymerization agent. The primers are preferably single stranded but may be double stranded. If the primers are double stranded, the strands are separated prior to the amplification reaction. The primers used in the present invention, are selected so that they are sufficiently complementary to the different strands of the sequence to be amplified that the primers are able to hybridize to the strands of the sequence under the amplification reaction conditions. Thus, noncomplementary bases or sequences can be included in the primers provided that the primers are sufficiently complementary to the sequence of interest to hybridize to the sequence.

The oligonucleotide primers can be prepared by methods which are well known in the art or can be isolated from a biological source. One method for synthesizing oligonucleotide primers on a solid support is disclosed in U.S. Pat. No. 4,458,068 the disclosure of which is herein incorporated by reference into the present application.

The term "PCR" refers to a polymerase chain reaction, which is a thermocyclic, polymerase-mediated, DNA amplification reaction. A PCR typically includes nucleic acids, oligonucleotide primers complementary to each strand of the nucleic acids, a thermostable DNA polymerase, and deoxyribonucleotides, and involves three distinct methods that are multiply repeated to effect the amplification of the original nucleic acid. The three methods (denaturation, hybridization, and primer extension) are often performed at distinct temperatures, and in distinct temporal steps. In many embodiments, however, the hybridization and primer extension methods can be performed concurrently.

A "nucleic acid" refers to a molecule of specific identity that can serve as a template for the synthesis of a complementary molecule.

The "nucleic acid" may be DNA or RNA, for example, double or single stranded DNA or RNA or a double stranded DNA-RNA hybrid and/or analogs and derivatives thereof. Specifically, a "nucleic acid" refers to the sequence between and including the two primers. The nucleic acid of specific sequence may be derived from any of a number of sources, including humans, mammals, vertebrates, insects, bacteria, fungi, plants, and viruses. In certain embodiments, the target nucleic acid is a nucleic acid whose presence or absence can be used for purposes including but no limited to medical or forensic purposes such as prognosis and/or diagnosis of a disease or a cancer, selective species isolation, DNA fingerprinting, etc. Any nucleic acid can be amplified using the present invention as long as a sufficient number of bases at both ends of the sequence are known so that oligonucleotide primers can be prepared which will hybridize to different strands of the sequence to be amplified. In the context of PCR, a "target nucleic acid" may represent a fragment or fraction of the nucleic acids added to the reaction. A "non-target nucleic acid" is the equivalent region of nucleic acid from another species, another gene in the same species or any other related source.

The term "deoxyribonucleoside triphosphates" refers to dATP, dCTP, dGTP, and dTTP or other analogues.

The term "polymerization agent" as used in the present application refers to any compound or system that can be used to synthesize a primer extension product. Suitable compounds include, but are not limited to, thermostable polymerases, *E. coli* DNA polymerase I, Klenow fragment of *E. coli* DNA polymerase I, T4 DNA polymerase, T7 DNA polymerase, *T. litoralis* DNA polymerase, and reverse transcriptase.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Non-limiting examples of thermostable polymerases include, Taq, Tth, Pfu, Vent, deep vent, U1Tma, and variations and derivatives thereof.

"*E. coli* polymerase I" refers to the DNA polymerase I holoenzyme of the bacterium *Escherichia coli*.

The "Klenow fragment" refers to the larger of two proteolytic fragments of DNA polymerase I holoenzyme, which fragment retains polymerase activity but which has lost the 5'-exonuclease activity associated with intact enzyme.

"T7 DNA polymerase" refers to a DNA polymerase enzyme from the bacteriophage T7.

An "amplicon" is a polynucleotide product generated in an amplification reaction.

Reference to "a mismatch" in the context of the present invention includes the case where a nucleotide in the inverted repeat region (head) of the primer does not or cannot pair through Watson-Crick base pairing with the corresponding nucleotide in the target amplicon derived from that part of the target nucleic acid corresponding to the internal sequence of the non-target nucleic acid (from which the inverted repeat region is derived). For example, adenine in the inverted repeat region would form a mismatch with adenine, cytosine, or guanine in the corresponding sequence in the target amplicon. In addition, a mismatch occurs when a first nucleotide cannot pair with a second nucleotide because the second nucleotide is absent (i.e., an unmatched nucleotide) or be the result of additional nucleotide(s). The inverted repeat region may contain more than one mismatches. The absent or additional nucleotides could be either in the head of the primer or in the internal sequence in the target nucleic acid In order that the present invention may be more readily understood, we provide the following non-limiting embodiments of the present invention.

For the purpose of allowing a better understanding of the present invention, but without wishing to limit the present invention in any way, the general principle of a preferred embodiment of the present invention is outlined in FIG. 1. A 5' extension ("head") is added to one or both of the primers used in PCR. The sequence of the head is an inverted repeat of an internal sequence within the amplicon; it is designed to match with the sequence whose amplification is to be suppressed but to mismatch significantly with sequences that it is desired to amplify.

When copied, the head gives rise to a 3' terminal sequence that is capable of self-priming due to its complementarity to the downstream sequence. This would give rise to a long hairpin loop structure that cannot be efficiently used as a template for further rounds of amplification causing inhibition of the amplification of the unwanted fragment.

If one primer contains such a head extension the PCR reaction includes three regions determining specificity of amplification—the forward and reverse priming sites and the head priming site. By including a head on both the forward and reverse primers, four regions of selectivity can be incorporated into a single PCR reaction.

Whilst the formation of hairpin structures that lead to synthesis of unexpectedly high molecular weight fragments has been observed previously (V Potaman BioTechniques 27 1110-1114 (1999)) hairpin structures have not been utilised to provide for selective amplification. A different application of hairpin priming, where priming occurs within the primer, has been used to suppress spurious "end-repair" priming in PCR walking (Devon et al, Nucleic Acids Res. 23:1644 (1995)). This does not involve head loop priming within the target sequence.

BRIEF DESCRIPTION OF THE DRAWINGS

FIG. 1 is a schematic drawing of amplification of a target sequence using an embodiment of the method of the invention;

FIG. 3 Diagram of EHL48 Headloop Priming (SEQ ID NOs:35, 36, 37 and 38).

FIG. 4 Mixtures of *E. coli* DNA with either *S. acidophilus* or *S. thermosulfooxidans* rDNA amplicons were prepared in the amounts shown above the panels. Amplifications used the reverse primer NR-R1i with either the non-selective forward primer NR-F1i or headloop primers EHL48, EHL64 or SAHL as indicated in the panels. In Panel A MgCl$_2$ was at 1.7 mM, primers at 200 nM. In Panel B MgCl$_2$ was at 1.3 mM, primers at 400 nM and for Panel C MgCl$_2$ at 1.5 mM, primers 400 nM. At the end of PCR reactions melting curve analysis was done by monitoring the change in SyberGreen fluorescence with increasing temperature (in an ABI Prism 7700 real time PCR instrument).

FIG. 5 All PCRs were done using primers SAHL and NR-R1i at 400 nM, with ratios of input rDNA amplicons as shown above the panels. Panel A shows the melting profiles of PCR products from reactions in which the MgCl$_2$ concentration was either 1.3 mM or 1.5 mM. In both Panels B and C the optimum MgCl$_2$ concentration of 1.3 mM was used. Panel D shows reactions done in the absence or in the presence of 0.6M betaine; MgCl$_2$ was at 1.5 mM. The lowering of the melting temperature in the presence of betaine is evident.

FIG. 12 is a comparison of amplification by control and headloop primers from genomic DNA mixture using Taqman detection of unmethylated PCR products, and FIG. 13 is the -sequence of the GSTP1 gene from 64 bases upstream to 96 bases downstream of the transcription start site, either unmodified (upper) (SEQ ID NO:30) or following bisulphite conversion and PCR amplification, assuming CpG sites are methylated (lower, B-M) (SEQ ID NO:31). Positions of CpG sites −7 to +10 are shown above the sequence. The position of forward primer F52A (SEQ ID NO:32) is shown (note the base mismatch at CpG site-3). The position of the base primers for the headloops Hlint5-10Ni (GSTintR11i) (SEQ ID NO:33) and Hlint5-10 and 5-10X (GSTintR1) (SEQ ID NO:34) are shown beneath their target sequences. The head regions for the primers are shown under their target sequences. For each headloop primer the head sequence joins to its primer part as shown by the arrows.

FIG. 15 PCR amplifications were done on plasmid mixes representing $10^6$ unmethylated: $10^3$ methylated molecules. Amplifications were done using F52A and the headloop primers Hlint5-10 and Hlint5-10Ni. Concentrations of MgCl₂ were as shown in the panels.

EXAMPLES

Example 1

Headloop PCR Selective for Different Bacterial 16S Ribosomal RNA Genes

Figure 2:
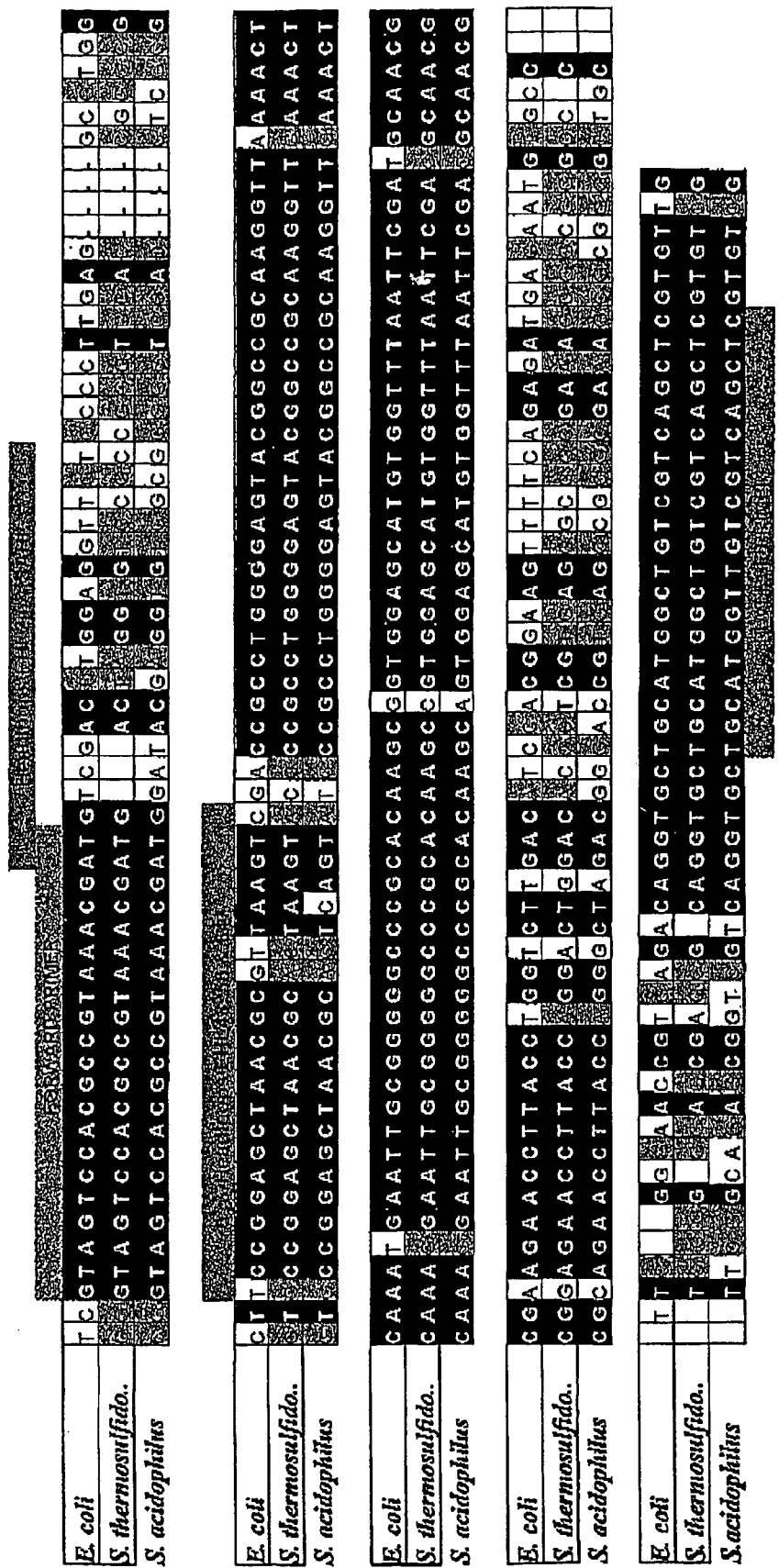
FIG. 2 shows sequences of the amplified region of the 16S ribosomal RNA genes from *E. coli* (SEQ ID NO:27), *S. acidophilus* (SEQ ID NO:29) and *Sulfobacillus thermosulfidooxidans* (SEQ ID NO:28) are aligned. Bases identical in all three species are shaded black and those identical in two of the three in grey. The sequences corresponding to the primers and to the headloop target regions are indicated.

Amplification of 16S ribosomal DNAs is often used in the identification of bacterial species and sequences of a large number of species have been determined. The presence of certain highly conserved regions has allowed the design of primer pairs for the amplification of essentially all bacterial ribosomal DNAs. FIG. 2 shows the sequences of the target region of 16S ribosomal RNAs of the bacterial species. *E. coli*, *Sulfolobulus acidophilus* and *Sulfolobulus thermosulfidooxidans* and the regions to which the "universal" primers, NR-R1i and NR-F1i, bind. The forward primer NR-L1i was used as the base for design of headloop primers for inhibition of amplification of DNA of either *E. coli* (EHL prefixes) or *S. acidophilus* rDNA (see Table). An example of headloop priming for the EHL48 primer (SEQ ID NO:35) is shown in FIG. 3. After the initial priming cycle, in a subsequent cycle extension of the reverse primer leads to incorporation of sequences complementary to the EHL48 "head" (SEQ ID NO:36) at the 3' end of the synthesised strand. These head sequences can loop back and anneal to their complementary target sequences (SEQ ID NOs:37 and 38) within the amplicon. The head forms a perfect match to the *E. coli* target sequences and so can prime and extend to form an extended hairpin loop structure. It is expected that such structures will be refractory to further amplification. For the *S. acidophilus* amplicon the head sequence has four mismatches to the complementary region, preventing priming and leaving the strand available for further rounds of PCR.

| PRIMER | ω HEAD | ω Priming region |
|---|---|---|
| NR-R1i | | GAG CTG ICG ACI ICC ATG CA (SEQ ID NO:1) |
| NR-F1i | | GTA GTC CII GCI ITA AAC GAT (SEQ ID NO:2) |
| EHL 48 | GACTTAACGCGTTAGCTC | GTA GTC CII GCI ITA AAC GAT (SEQ ID NO:3) |
| EHL 64 | GACTTAACGCGTTAG CTCCGGA | GTA GTC CII GCI ITA AAC GAT (SEQ ID NO:4) |
| EHL2a | ACAACCTCCAAGTCGACAT | GTA GTC CII GCI ITA AAC GAT (SEQ ID NO:5) |
| SAHL | CGACACCTCGTATCCAT | GTA GTC CII GCI ITA AAC GAT (SEQ ID NO:6) |

I = inosine (In the above table, head and priming region are shown separately, however it will be clear that the head is 5' to the primer region and contiguous with it.)

Standard PCR reactions were set up in 25 ul containing

| 2× PCR master Mix (Promega) | 12.5 µl |
|---|---|
| Forward primer (400 nM final) | 1.0 µl |
| Reverse primer (400 nM final) | 1.0 µl |
| DNA | 1.0 µl |
| SyberGreen (1:1000 dilution of stock) | 0.2 µl |
| Water | 9.5 µl |

Reactions were run on an Applied Biosystems ABI Prism 7700 instrument with the following cycling conditions.

| 95° | 1 min | |
|---|---|---|
| 95° | 30 sec | } 40 cycles |
| 58° | 30 sec | |
| 72° | 30 sec | |

Following the amplification cycles the melting profile of reaction products was determined by measuring the change in SyberGreen fluorescence as the temperature was raised from 60° C. to 100° C. over 20 minutes.

Suppression of *E. coli* rDNA Amplification

Mixtures of *E. coli* DNA with DNA of either *S. acidophilus* or *S. thermosulfooxidans* were amplified using the non-selective primers NR-F1i and NR-R1i, or with the headloop primers EHL48 or EHL68 and reverse primer NR-R1i (FIG. 4). Amplification products were analysed by determining their melting profiles—the *E. coli* rDNA product melts at about 77°-78° C., while both *S. acidophilus* and *S. thermosulfidooxidans* amplicons melt at about 91° C. Note that the control PCR product is shorter than the headloop PCR products and so melts at a slightly lower temperature; slight differences due to tube position in the block are also seen.

Starting with a 1:1 mix of DNAs the ratio of PCR products was about 1:2 for *E. coli*:*S. acidophilus* when non-selective primers were used. Both the EHL48 and EHL64 headloop primers effectively inhibited amplification of the *E. coli* amplicon as the melting curve of products showed only the presence of the *S. acidophilus* rDNA (Panel A). Likewise EHL48 effectively suppressed amplification of *E. coli* rDNA in the presence of an equal amount of *S. thermosulfidooxidans* DNA (Panel B). When the ratio of DNAs was increased to 50:1 (Panel C), substantial enrichment of the *S. thermosulfidooxidans* amplicon was seen. Another headloop primer, EHL2a, that targets sequences adjacent to the PCR priming site showed a greater level of enrichment of *S. thermosulfidooxidans* DNA; the melting profile in the region of the *E. coli* DNA indicates formation of aberrant DNA structures.

The headloop primer SAHL (SEQ ID NO:6) that targets the same region as EHL48 (SEQ ID NO:3) and EHL64 (SEQ ID NO:4), but is designed to anneal with and prime on the *S. acidophilus* sequence (SEQ ID NO:28) was also tested for its capacity to suppress amplification of the *S. acidophilus* rDNA (Panel D). Starting with a 50:1 mix of *S. acidophilus* to *E. coli* rDNA, amplification of *S. acidophilus* DNA was strongly suppressed and products showed a slight excess of the *E. coli* amplicon.

Effects of Magnesium Concentration and Betaine on Headloop Suppression PCR

In optimizing a number of headloop PCRs, we noticed that the selectivity of amplification was improved if the final concentration of free $Mg^{2+}$ was lowered. In the example shown in FIG. 5, the selectivity of amplification of *E. coli* DNA in the presence of a fifty-fold excess of *S. acidophilus* DNA using the SAHL headloop primer is significantly improved when the $Mg^{2+}$ concentration is lowered from 1.5 mM to 1.3 mM. The sum concentration of dNTPs in the reaction was 0.8 mM, leaving a free $Mg^2$ concentration of 0.5 mM. The free $Mg^{2+}$ concentration can also be below 0.7 mM or 0.5 mM or less. For this amplification, lowering of the free $Mg^{2+}$ further to 0.3 mM inhibited any amplification. In Panels B and C, detection of *E. coli* rDNA in the presence of 250 and 500-fold excesses of *S. acidophilus* rDNA is shown.

Betaine has been previously shown to improve the amplification of G+C rich DNAs. Addition of betaine was also found to increase the selectivity of headloop PCR. In FIG. 3, Panel D, the proportion of the *E. coli* amplicon is significantly increased in the reaction containing 0.6 M betaine. A useful range of betaine is about 400 mM to about 1.2 M.

These examples demonstrate the function of headloop PCR primers in suppressing amplification of chosen target DNAs, either E, coli or *S. acidophilus* 16S rDNA, and demonstrate effectiveness of headloop suppression with target regions adjacent to the PCR priming site and up to 40 bases away.

Example 2

Headloop PCR Selective for Methylated DNA

To analyse or detect methylation of DNA, it is first treated with bisulphite, a procedure that results in the conversion of C's to U's (and thus ultimately to T's after copying). However, any C's that are methylated (normally at CpG positions) are resistant to this conversion. Because the methylated and unmethylated forms of a DNA fragment will now have different sequences, it is possible to design primers that specifically amplify the methylated form.

The sections of the primers used here responsible for priming are designed to work on both methylated and unmethylated forms of the DNA, with no bias. To achieve this, regions of the target DNA fragment that lack CpG's are chosen. In such regions, the DNA sequence that results from bisulphite conversion will be the same regardless of the overall methylation status of the fragments.

Selective enrichment of the methylated form is achieved by the inclusion of a 5' extension in one or both of the primers used in the PCR. The sequence of the head is an inverted repeat of a downstream sequence in the DNA fragment that is to be selected against. When copied the head gives rise to a 3' terminal sequence that is capable of self-priming due to its complementarity to the downstream sequence. This gives rise to long hairpin loop structure that is not expected to be efficiently used as template for further rounds of amplification, causing inhibition of the amplification of the unwanted fragment. The head sequence is designed to be an inverted repeat of a downstream sequence expected to result from the bisulphite conversion of an unmethylated DNA fragment. After incorporation the added sequence causes self-priming on fragments derived from unmethylated DNA, leading to inhibition of the amplification of unmethylated fragments. Because the downstream sequence is chosen to contain several CpG sites (at which bisulphite conversion does not occur in the case of methylated DNA) there is insufficient complementarity to allow self-priming and thus little or no inhibition of the amplification of the 'methylated' DNA fragments.

Plasmids Used in these Experiments:

The plasmids #77 and #58 were used in this work. They resulted from the insertion into pGEM-T (Promega) of PCR products derived from the amplification of a GST fragments from bisulphite-treated human. The sequences of the inserts in these plasmids are shown below.

```
#77 'Methylated GST fragment' or 'M'

CGGGATCGTAGCGGTtTTAGGGAATTTttttttCGCGATGTt
 tCGGCGCGttAGTTCGtTGCGtAtAtTTCGtTGCGGTttTt
 TTtTGtTGTtTGTTTAtTtttTAGGtttCGtTGGGGAttT
 GGGAAAGAGGGAAAGGtTTtttCGGttAGtTGCGCGGCGAt
 TtCGGGGAtTttAGGGCGttttTtTGCGGtCGACGttCGGG GTGtAGCGGtCGtCGGGGtTGGGGtCGGCGGGAGTtCGCGG
GAtttTttAGAAGAGCGGtCGGCGtCGTGAtTtAGtAtTGG
GGCGGAGCGGGGCGGGAttAtttTTATAAGGtTCGGAGGtC
GCGGAGtETTCGtTGGAGTTTCGtCGtCGtAGTtTTCGttA
ttAGTGAGTACGCGCGGttCGCGTtttC   (SEQ ID NO:7)
```

This sequence corresponds to the sequence expected to result from amplification of bisulphite-treated human GST fragment when the DNA is methylated at CpG positions. For simplicity, referred to as 'Methylated DNA'.

The full sequence of the insert is shown. The first CpG in the DNA fragment is −41 and the last (most 3' in the diagram) is CpG+10.

```
#158 'Unmethylated GST fragment' or 'U'
    -39
 t GGTtTTAGGGAATTTtttttt tGtGATGTtttGGtGtGtT
    Primer F2
      LUHF2 Head     AAAACACTACAAAACCACA<
                     (SEQ ID NO:40)
      CLUHF2 Head    AAAACACTACAAAACCACAC<
                     (SEQ ID NO:41)
      FTF2 Head      AAAACACTACAAAACCACACAA
                     (SEQ ID NO:42)
 AGTTtGtTGtGtAtAtTTtGtTGtGGTtttTtTTtTGtTG
                -29
 TtTGTTTAtTtttTAGGttttG tTGGGGATtTGGGAAAG A
                        Primer R1T
 (SEQ ID NO:8)
```

This sequence corresponds to the sequence expected to result from amplification of bisulphite-treated human GST fragment when the DNA is not methylated at CpG positions. For simplicity, referred to here as 'unmethylated' DNA. The sequence of the insert within the amplified region is shown, from CpG site −39 to −29. Sequences of the forward primer F2 and the reverse primer R1T target region are boxed. The head portions of the headloop primers LUH F2, CLUH F2 and FT F2 are shown beneath their inverse complement sequences. Symbols used in the sequences are—

T: T residue in the original sequence t: T residue expected to result from bisulphite conversion of a C residue in the original sequence.

C: C residue that was methylated (because part of a CpG sequence) and thus resistant to conversion by bisulphite treatment.

t: T residue resulting from conversion of a C that was unmethylated despite being in a CpG sequence.

Primers Used:

Conversion-Specific Primers

Conversion-specific primers are designed to regions that include several converted t's (arising from conversion of C's) so that they will selectively amplify DNA fragments that have been successfully converted by the bisulphite treatment. By avoiding regions containing CpG sites these primers should be able to amplify DNA fragments regardless of their methylation status at CpG residues, i.e. both methylated and unmethylated forms of the fragment should be amplified equally well.

F2: 5' GGTtTTAGGGAATTTtttttt (SEQ ID NO:9)

R1T: 5' CACCTTTCCCAaaTCCCCAa (SEQ ID NO:10)

Bases (a & t) in lower case correspond to converted C's in original sequence.

The regions to which these primers hybridize to the target fragment are boxed in the diagram above. The regions to which the primers bind are identical in the methylated and unmethylated forms of the DNA fragment.

Headloop Primers:

Selection against the unmethylated form of the fragment is achieved by including a special 5' extension in one or both primers. To show clear proof of principle only one primer was made with the special 5' extension. Obviously if both primers are modified then any effect reported here would be expected to be greatly magnified. F2 was chosen as the primer to modify for these tests. 5' extensions (boxed) were added to the F2 primer as shown below:

```
LUH F2
       aCaCCaaaACATCaCaaaa GGTTtTAGGGAATTTtttttt
                                (SEQ ID NO:11)
CLUH F2
       CaCaCCaaaACATCaCaaaa GGTTtTAGGGAATTTtttttt
                                (SEQ ID NO:12)
CLUR F2
       CCATCAACAAAAAACACACA GGTTtTAGGGAATTTtttttt
                                (SEQ ID NO:13)
FT F2
       AACaCaCCaaaACATCaCaaaa GGTTtTAGGGAATTTtttttt
                                (SEQ ID NO:14)
```

LUH F2, CLUH F2 and FT F2 all have 5' extensions that are an inverse repeat of a sequence within the unmethylated DNA fragment. Thus for LUH F2 the 5' extension of aCaCCaaaACATCaCaaaa (SEQ ID NO:15)

targets the ttttGtGATGTtttGGtGt (SEQ ID NO:16)

sequence downstream of the F2 priming site. Bases are shown as:

A: A complementary to T in original sequence a: A complementary to converted C (U) in original sequence, not part of CpG site.

a: A complementary to converted C (U) in original sequence, part of CpG site.

The CLUR F2 primer is a control. It has the same number of A's, C's and T's in its 5' extension as has CLUH F2, but in an order that does not match any sequence within the relevant region of the GST gene.

Method

Real time PCR was done using an Applied Biosystems 7700 machine. The same 'reverse' primer R1T was used throughout. Amplification was monitored using Sybergreen.

The reverse primer R1T was used at 1 μM. F2 was used at 200 nM. All of the other primers were used at 40 nM. The hot start system based on Platinum Taq Polymerase (Invitrogen) and buffer supplied were used.

DNA input:

M=$10^6$ molecules of #77, methylated plasmid

U=$10^8$ molecules of #58, unmethylated plasmid

M*U $10^4$ #77 plus 108 #58 (mixture, 10,000× excess of unmethylated plasmid).

Results

Figure 6:
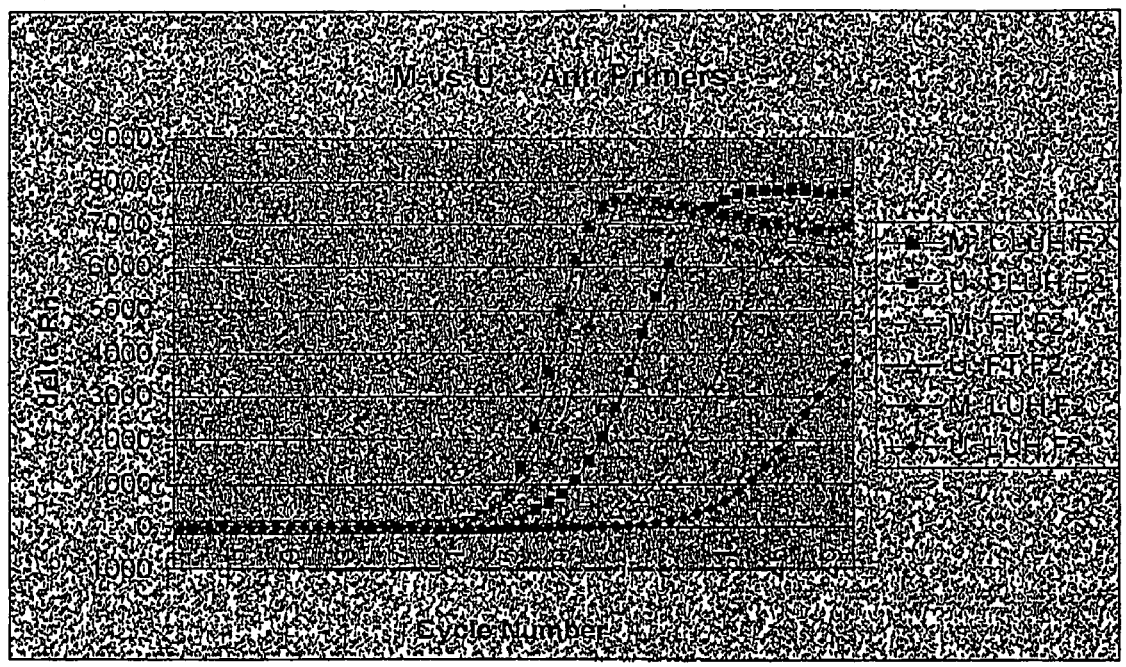
FIG. 6 shows amplification of either methylated or unmethylated plasmid DNA using different headloop primers.
Figure 7:
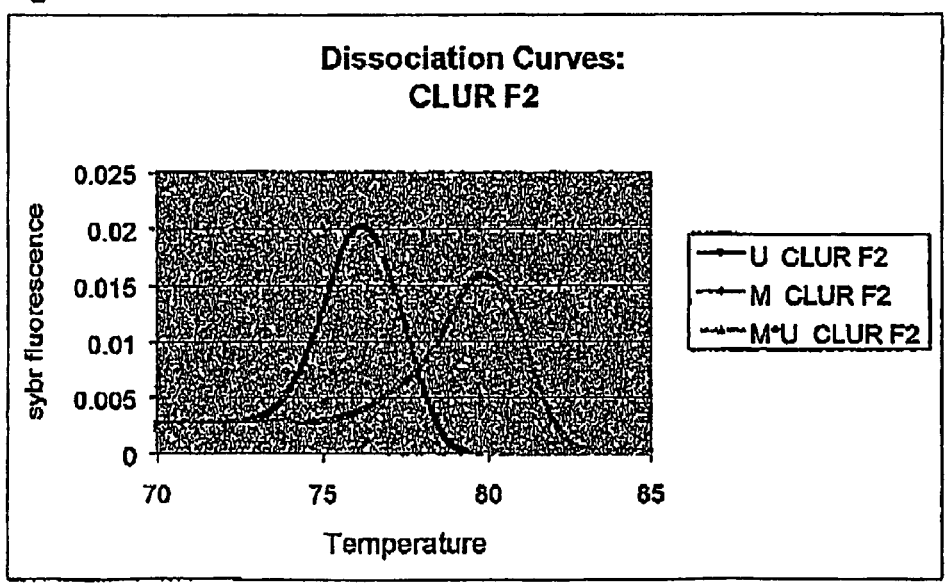
FIG. 7 shows dissociation curves of PCR products obtained from methylated, unmethylated and a mixture of DNAs using the control CLUR-F2 primer.

Methylated ($10^6$ molecules) or unmethylated ($10^8$ molecules) plasmid was used in PCR reactions with the three different headloop primers, LUH-F2, CLUH-F2 and FT-F2 in combination with the reverse primer R1T and amplification monitored with Sybergreen (FIG. 6). All three primers amplified the methylated plasmid with similar efficiency. With unmethylated plasmid the appearance of PCR product was significantly delayed despite the use of 100 fold more plasmid in reactions. Primers LUH-F2 and FT-F2 gave the greatest differential in amplification between methylated and unmethylated DNA. When either the short bisulphite conversion-specific primer F2 or the primer CLUR-F2 that contains an unrelated 5' extension sequence were used in combination with R1T as the reverse primer, both methylated and unmethylated sequences were amplified. Amplification products obtained using primers CLUR-F2 and R1T were assessed by melting curve analysis; their dissociation curves are shown in FIG. 7.

The samples were heated and the reduction in Sybergreen fluorescence that occurs when the DNA strands separate was monitored. The two forms of amplified DNA can be distinguished because of a difference in melting temperature; the unmethylated fragment is less GC rich and thus melts at a lower temperature, ~76° C., than the methylated DNA ~80° C. The mixture of plasmids (10000× excess of unmethylated) gives a PCR product similar to that given by the unmethylated plasmid, indicating that as expected the 'unmethylated' product predominates. Note that position of sample in the Applied Biosystems 7700 block affects results slightly, so positions of melting curve peaks are not expected to be identical even in duplicate samples.

Figure 8:
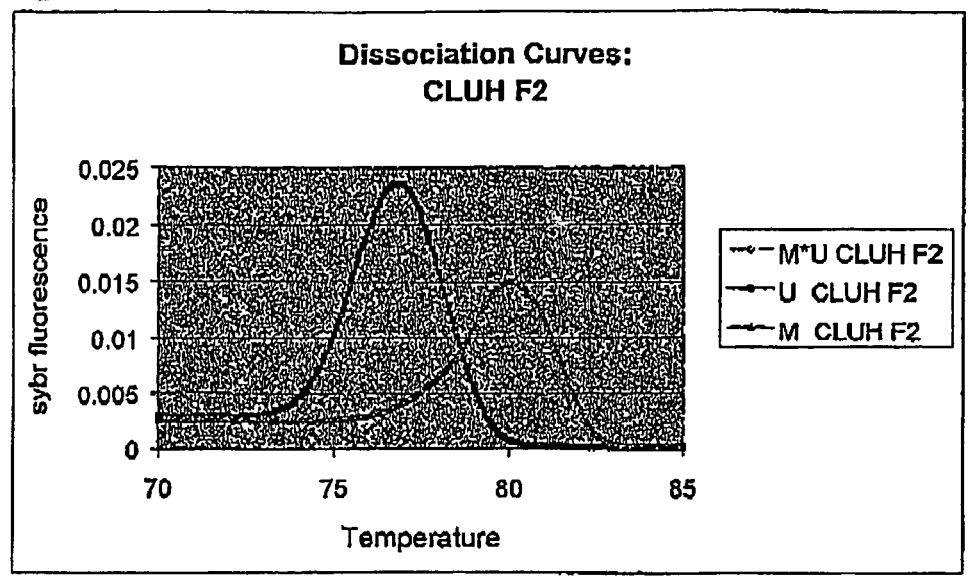
FIG. 8 shows dissociation curves of PCR products obtained from methylated, unmethylated and a mixture of DNAs using the headloop CLUH-F2 primer.

The equivalent experiment was repeated using the headloop primer CLUH-F2 since it has the same length extension as CLUR-F2 (FIG. 8). Separate amplifications of methylated and unmethylated plasmids produced PCR products with the expected dissociation curves. The product of amplification of a 10,000:1 mixture of unmethylated and methylated plasmids dissociated with a melting curve indicative of a mixture of methylated and unmethylated DNA, with methylated DNA predominating. Thus, the methylated form is successfully amplified despite the initial presence of an excess of 10,000 fold of the unmethylated plasmid.

Use of Taqman Probes to Confirm Efficacy of Headloop Primers

Taqman probes allow monitoring of PCR products during amplification. Probes selective for detection of methylated and unmethylated GSTP1 sequences were prepared.

Probe PRB M

5' FAM TTGCGTATATTTCGTTGCGGTTTTTTTTT TAMRA
(SEQ ID NO:17)

This is a Taqman probe, designed to be cleaved during a PCR if it is able to hybridize to the amplified product. Cleavage results in an increase in fluorescence of the FAM dye.

FAM=Carboxyfluorescein,
TAMRA=Carboxytetramethylrhodamine

Probe PRB U

5' TET TTGTGTATATTTTGTTGTGGTTTTTTTTTTGTTG TAMRA (SEQ ID NO:18)

This is a Taqman probe, designed to be cleaved during a PCR if it is able to hybridize to the amplified product. Cleavage results in an increase in fluorescence of the TET dye.

TET=Tetrachlorofluorescein,
TAMRA=Carboxytetramethylrhodamine

Results

Figure 9:
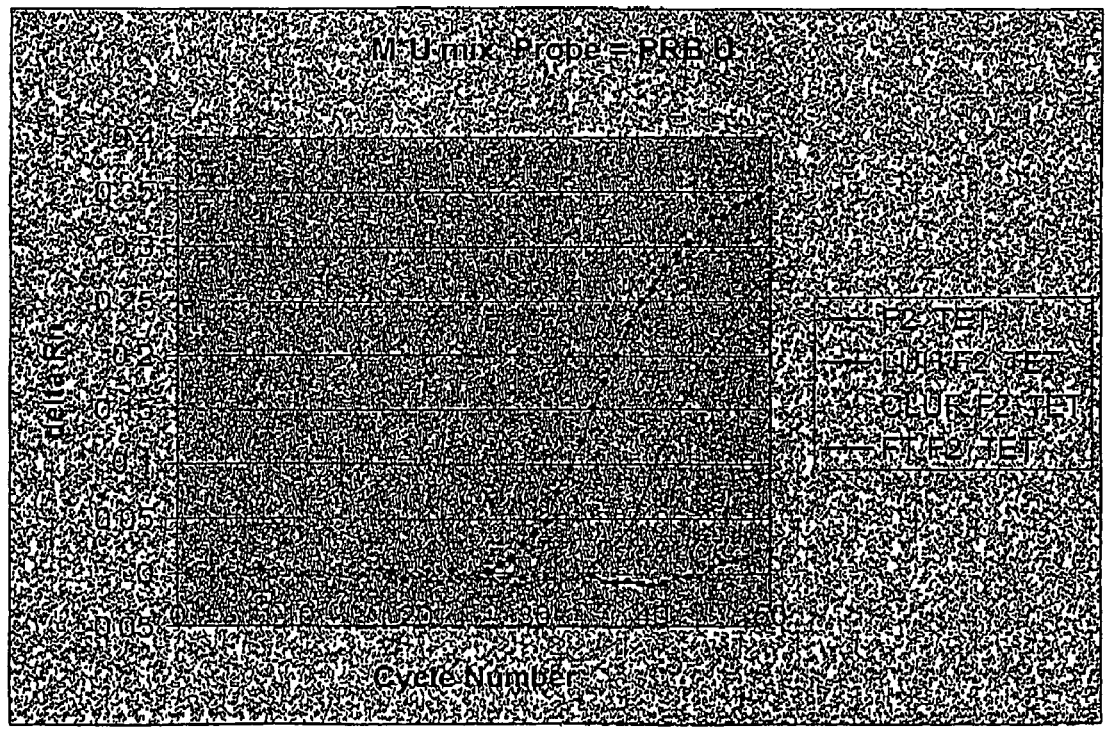
FIG. 9 is a comparison of amplification by control and headloop primers from plasmid DNA mixtures using Taqman detection of unmethylated PCR products.
Figure 10:
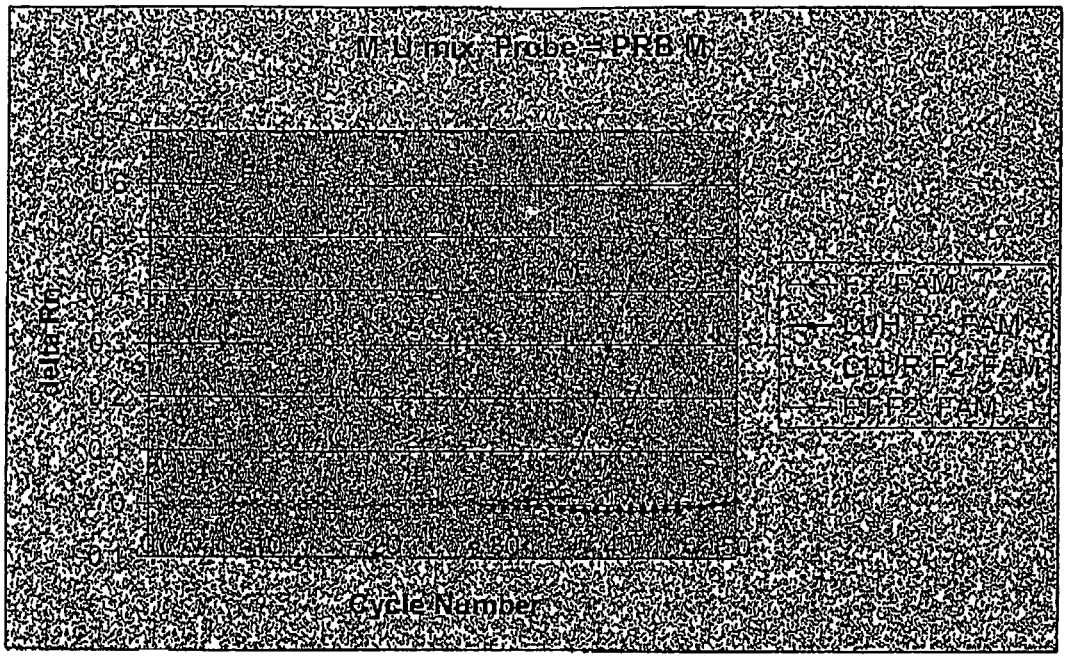
FIG. 10 is a comparison of amplification by control and headloop primers from plasmid DNA mixture using Taqman detection of methylated PCR products.

Mixtures of unmethylated and methylated plasmids were amplified using control, conversion-specific, primers F2 and CLUR-F2 or the two headloop primers, LUH-F2 and FT-F2, in combination with the R1T reverse primer. Amplification of unmethylated and methylated products was monitored using the PRB-U and PRB-M probes (FIGS. 9 and 10). Amplification of unmethylated DNA is substantially (FT-F2) or almost completely (LUH-F2) suppressed, compared with the control primers.

As shown in FIG. 10, when the amplification of methylated DNA is detected by using PRB M, it is clear that methylated DNA is selectively amplified by the test primers LUH F2 and FT F2, even though the original input DNA contained a 10,000 fold excess of unmethylated form. Using the control primers methylated DNA is not detected since it forms such a small proportion of the product.

Example 3

Amplification from Bisulphite-Treated Genomic DNA

DNA was isolated from LNCaP prostate cancer cells in which the GSTP1 gene is methylated and from Placenta that is expected to be unmethylated in the GSTP1 gene.

Bisulphite-treated DNA from LNCaP and Placenta was amplified by primers that lie outside the region of interest. The primers GSATA56 (: GTTTTGTGAAGAGGGTGTG-TAAGTTT) (SEQ ID NO:19) and R4 (AAAACCTTTC-CCTCTTTCCCAAA) (SEQ ID NO:20) were designed to amplify bisulphite-treated DNA regardless of methylation status and lie outside the region amplified by the headloop primers and R1T.

A mixture of the two can be used to mimic the situation in which a small amount of tumour-derived DNA (methylated GSTP1) might need to be detected despite the presence of an excess of normal (unmethylated GSTP1) DNA. The mixture used in the following experiment was referred to as 'LP(1: 100).): 1/10,000 dilution of 1$^{st}$ round PCR product amplified using GSTAS56 and R4 from bisulphite-treated LNCaP DNA plus 1/100 dilution of 1$^{st}$ round PCR product amplified using GSTAS56 and R4 from bisulphite-treated Placental DNA.

Figure 11:
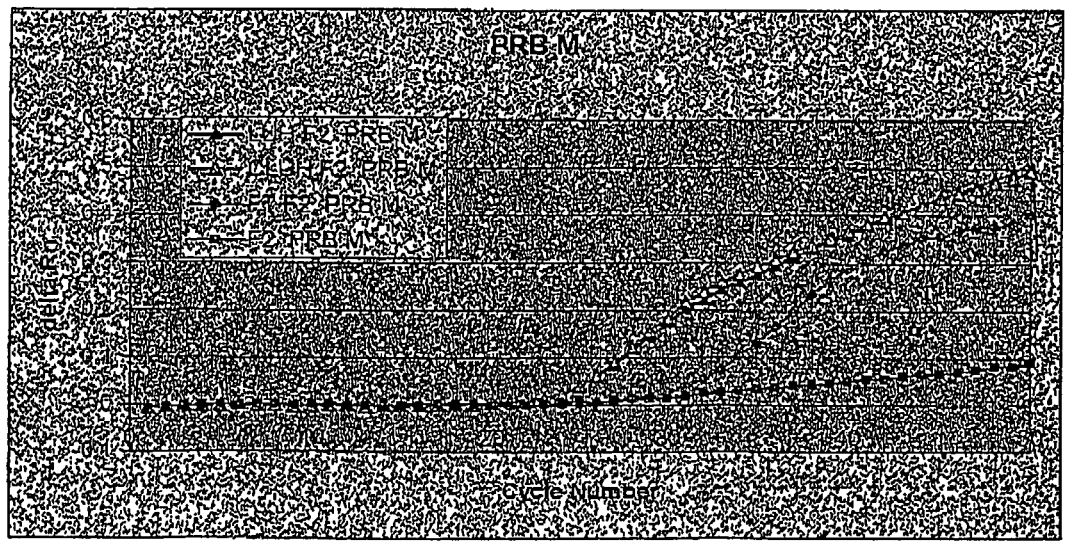
FIG. 11 is a comparison of amplification by control and headloop primers from genomic DNA mixture using Taqman detection of methylated PCR products.

This mixture was used as input for a Real-time PCR experiment designed to show how the new primers allow sufficient enrichment of methylated DNA for detection despite the starting material having a large excess of unmethylated DNA. The results are shown in FIGS. 11 and 12.

When the control primer F2 is used, almost all product is derived from the unmethylated DNA (as detected by PRB U). However, when the headloop primers with the 5' extensions are used, the methylated DNA is selectively amplified and only low levels of unmethylated DNA are made.

Example 4

Headloop Suppression PCR on a Second Region of the GSTP1 Gene

Headloop primers were designed to bisulphite-treated DNA of a region within the transcribed sequences of the GSTP1 gene. Sequences of the primers are shown in the table below. Inosine is included in primers GSTR11i and GSTH-Lint5-10Ni at a position corresponding to a CpG site at which the bisulphite-converted DNA may be either a C or U depending on the state of methylation. Similarly the F52A primer contains a deliberate mismatch (A) at the position of a C in a CpG site so as not to bias amplification of methylated or unmethylated DNA.

| PRIMER | ω HEAD | ω Priming region |
|---|---|---|
| F52A | | GGGATTATTTTTATAAGGTTAGGAGGT (SEQ ID NO:21) |
| GSTintR1 | | CCCATACTAAAAACTCTAAACCCCAT (SEQ ID NO:22) |
| HLint5-10 | TGTGTGGTTTGTGTTTTTG | CCCATACTAAAAACTCTAAACCCCAT (SEQ ID NO:23) |
| HLint5-10X | TGTGTGGTTTGTGTTTTTGGGGATG | CCCATACTAAAAACTCTAAACCCCAT (SEQ ID NO:24) |
| GSTintR11i | | CTCTAAACCCCATCCCCIAAA (SEQ ID NO:25) |
| HLint5-10Ni | TGTGTGGTTTGTGTTTTTG | CTCTAAACCCCATCCCCIAAA (SEQ ID NO:26) |

I = inosine

All PCR reactions used F52A as the forward primer. Headloop primers use either GSTintR1 (HLint5-10 and HLint5-10X) or GSTintR11i (HLint5-10Ni). The position of the primers is shown on the sequence of this region of the GSTP1 gene in FIG. 13. PCR using these primers was used to identify factors contributing to optimal selective amplification using headloop primers. Primers were at a final concentration of 200 nM and other reaction components as described above. PCR cycling conditions, unless otherwise indicated were:

| | | |
|---|---|---|
| 95° | 2 min | |
| 95° | 15 sec | } 50 cycles |
| 60° | 1 min | | followed by dissociation curve analysis over 20 minutes across the temperature range 60° C. to 95° C.

Figure 14:
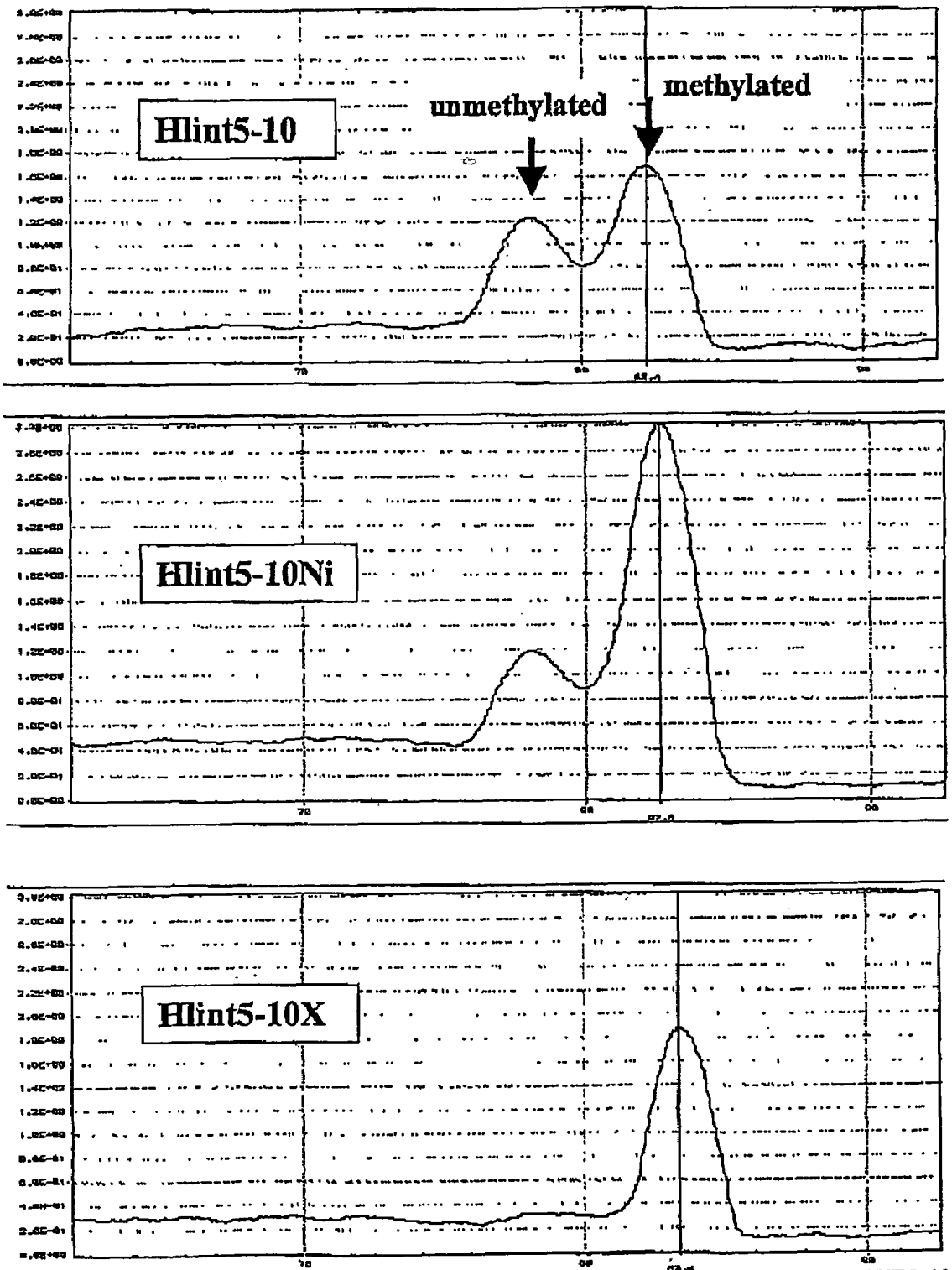
FIG. 14 A mix of two plasmids encompassing the region to be amplified and derived from methylated and unmethylated bisulphite-treated DNA was prepared in a ratio of 1000 unmethylated:1 methylated molecule. Amplifications were done using F52A and the headloop primer shown; cycling conditions as described in the text with MgCl₂ at 1.1 mM. Melting curve profiles are shown; the peak corresponding to the methylated sequence is to the right.

The efficacy of the three headloop primers was compared using plasmid DNAs derived from cloning of amplified bisulphite-treated DNA and corresponding to either methylated or unmethylated GSTP1 sequences. Plasmid DNAs were mixed in a ratio of $10^7$ unmethylated:$10^4$ methylated molecules and amplified using the different headloop primers in combination with the F52A forward primer (FIG. 14). Enrichment of 1000 fold or more for the methylated sequences was seen with the three headloop primers, with HLint5-10X showing the greatest level of suppression of amplification of unmethylated sequences.

The effect of varying the concentration of $Mg^{2+}$ ions is shown in FIG. 15. Amplifications using either HLint5-10Ni or HLint5-10X were done in the presence of 1.1, 1.3 or 1.5 mM $MgCl_2$. In both cases there was a concentration-dependent improvement in selectivity with decreasing levels of $MgCl_2$. This effect has been seen with a number of different headloop primers. Optimal headloop selectivity is consistently seen at the lowest $Mg^{2+}$ levels used that allow PCR amplification of the target sequences. In most cases this has corresponded to a level of free $Mg^{2+}$ ions of 0.3 mM.

Figure 16:
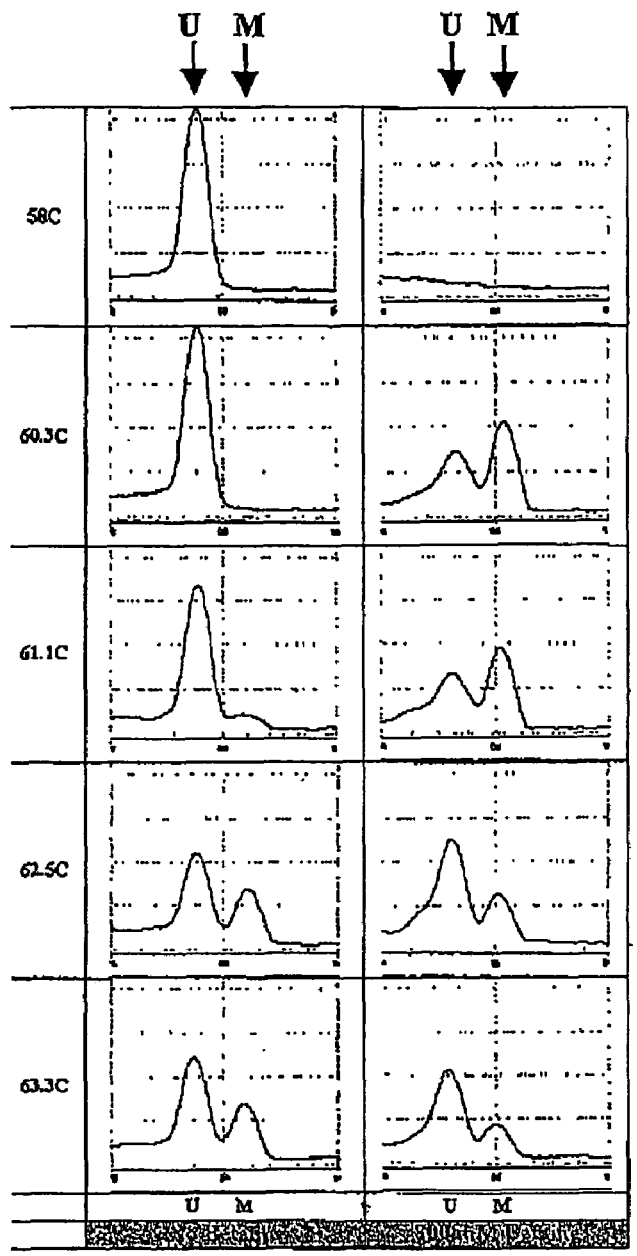
FIG. 16 PCR amplifications using F52A and the headloop primer Hlint5-10 were done on plasmid mixes representing 106 unmethylated: 103 methylated molecules. Amplifications were done in an Eppendorf Mastercycler temperature gradient PCR machine and denaturation profiles of the PCR products analysed in an Applied Biosystems ABI 7700 instrument. Denaturation profiles of PCR products from reactions done at the indicated temperatures and either in the absence or presence of 800 mM betaine are shown.

Betaine was shown to improve the selectivity of headloop amplification of 16S ribosomal RNA gene sequences. The effects of betaine and variation of the annealing/extension temperature on selective amplification of methylated and unmethylated sequences from bisulphite-treated DNA are shown in FIG. 16. Betaine at 0.8M substantially improves selectivity of headloop PCR; the optimal effects of betaine are seen across the range of 0.6 to 1.2 M. The effectiveness of the HLint5-10 headloop is also seen to depend on the annealing/elongation temperature.

Figure 17:
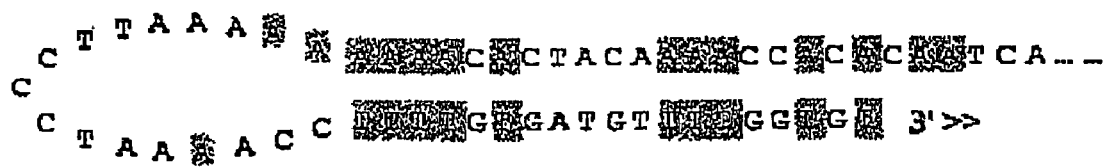
FIG. 17 is a schematic of loopback priming on "unmethylated" DNA following copying of primer LUH-F2 during reverse strand synthesis (SEQ ID NO:39).

Discussion:

The principle of suppression of PCR amplification through headloop priming is shown diagrammatically in FIG. 1 and with specific sequence examples in FIGS. 3 and 17. After the 5' extension becomes incorporated and then copied, a 3' end is produced that is capable of base-pairing with a region downstream in the same DNA strand, as shown. The efficiency of this base-pairing and priming is expected to depend on the length and sequence composition of the head region and the exactness of its match to the internal sequence within the amplicon. For the EHL48 headloop primer, the difference in complementarity between the *E. coli* sequence (perfect match) and the *S. acidophilus* amplicon (4 mismatches) is sufficient to provide for selective amplification of the *S. acidophilus* rDNA. For the LUHF2 headloop primer (FIG. 17) those bases underlined in the downstream region correspond to potentially methylated C's in CpG sequences in the original fragment. In the case of CpG-methylated DNA, the underlined positions would contain G's rather than A's in the downstream position, and no intramolecular duplex would be expected to occur.

If the structures shown schematically in FIGS. 3 and 17 are able to form during a PCR it is reasonable to assume that extension will occur from the base-paired 3' end, leading to single-stranded fragments that that have long inverted repeats. Such fragments are likely to form a hairpin loop by 'snapback' after denaturation, before a primer is able to hybridize, thus preventing synthesis of fresh copies and amplification of the fragments. Because formation of the hairpin structure is dependent on efficient headloop annealing and priming, sequences that share the same base primers but do not match sufficiently with the incorporated head sequences will continue to be amplified. For selective amplification of methylated DNA as shown in the experiments reported above, efficient headloop priming and suppression of amplification occurs only for the unmethylated form. For selective amplification of methylated DNA, the headloop primer method can be used separately or may be combined with other methods for selective amplification, such as "methylation specific PCR" (Herman et al., Proc Natl Acad Sci USA. 93: 9821-6 (1996)).

In the examples shown the position of the target sequences within the amplicon has varied with respect to the position of the primer on which the head forms an extension. In the case of the EHL48 and EHL64 headloop primers the target region for headloop priming was about 40 bases downstream of the base primer. For other headloop primers the target sequence was close to the priming end of the base primer (Hlint5-10) or overlapped the primer by 3 to 5 bases (EHL2a, SAHL, LUHF2, CLUHF2, FTF2, Hlint5-10Ni and Hlint5-10X).

For a number of headloop primers we have identified that the selectivity of amplification is improved at lower concentrations of free $Mg^{2+}$ ions, or in the presence of betaine. Selectivity can also be improved by lowering the concentration of the headloop primer. Other reaction conditions such as annealing temperature (FIG. 16), cycling times and buffer components may also alter the efficiency of headloop PCR.

Experiments described have involved addition of the 5' head extensions to just one of the primer pair resulting in three points of specificity in the PCR. It is possible to incorporate heads on both forward and reverse primers, providing four points of specificity, increasing selectivity further.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Furthermore, any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

Finally, it will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for the selective amplification of a target nucleic acid in a sample comprising the target nucleic acid and at least one non-target nucleic acid, the method comprising selectively amplifying the target nucleic acid compared to the at least one non-target nucleic acid by means of forward and reverse oligonucleotide primers, the forward primer comprising:
   a primer region that can prime and extend on the target and non-target nucleic acids; and
   a region that is an inverted repeat of an internal sequence of an amplicon of the at least one non-target nucleic acid but which contains at least one mismatch to the corresponding internal sequence of an amplicon of the target nucleic acid, the inverted repeat region being 5' of the primer region;
   wherein during amplification the forward primer extends on the target nucleic acid and the at least one non-target nucleic acid to give rise to first strand products and the reverse primer extends the first strand products to give rise to second strand products; and
   wherein the inverted repeat region located 5' of the primer region of the forward primer is copied during second strand synthesis to form a 3' terminal sequence within the second strand products; and
   wherein the 3' terminal sequence of the second strand product corresponding to the at least one non-target nucleic acid anneals to an upstream region of the same product corresponding to the internal sequence of the amplicon and is extended to form a hairpin loop structure that inhibits further amplification of the non-target nucleic acid.

2. The method according to claim 1, wherein the amplification step uses at least one reverse primer comprising the primer region and inverted repeat region.

3. The method according to claim 1, wherein amplification is by PCR.

4. The method according to claim 3, wherein the amplification technique is real time PCR.

5. The method according to claim 1, wherein the forward primer, excluding the inverted repeat region, is about 15 to 35 base units in length.

6. The method according to claim 1, wherein the inverted repeat region of the forward primer is about 5 to 30 base units in length.

7. The method according to claim 1, wherein the selectivity of amplification is controlled by carrying out amplification at a preselected free $Mg^{2+}$ concentration.

8. The method according to claim 1, wherein the amplification is carried out in the presence of free $Mg^{2+}$ at a concentration below about 0.7 mM.

9. The method of claim 7, wherein the free $Mg^{2+}$ concentration is about 0.5 mM or less.

10. The method according to claim 9, wherein the free $Mg^{2+}$ concentration is about 0.3 mM.

11. The method according to claim 1, wherein the amplification is carried out in the presence of betaine.

12. The method according to claim 11, wherein the betaine is present in an amount of from about 400 mM to about 1.2 M.

13. A method of selectively amplifying nucleic acid of a pre-selected species of organism from a mixture of one or more species of organism, the method comprising the steps of:
   (a) performing selective amplification of an isolated nucleic acid sample comprising nucleic acid isolated from a mixture of one or more species of organism in the presence of forward and reverse oligonucleotide primers, wherein the forward primer comprises:
   a primer region that can prime and extend on nucleic acid that is substantially conserved across a range of organism species; and
   an inverted repeat region of a non-conserved sequence characteristic of a pre-selected species present in an internal region of an amplicon produced from nucleic acids of said pre-selected species of organism, the inverted repeat region being 5' of the primer region;
   wherein during amplification the forward primer extends on the nucleic acid to give rise to first strand products and the reverse primer extends on the first strand products to give rise to second strand products; and
   wherein the inverted repeat region located 5' of the primer region of the forward primer is copied during second strand synthesis to form a 3' terminal sequence within the second strand products; and
   wherein the 3' terminal sequence of the second strand product corresponding to nucleic acid characteristic of said one or more species of organism anneals to an upstream region within the same product corresponding to the amplicon of the internal sequence and is extended to form a hairpin loop structure that inhibits further amplification of the nucleic acid from said one or more species of organism;
   (b) determining the presence of the amplified product; thereby
   (c) detecting the presence of a pre-selected species of organism based on the presence of the amplified product.

14. The method according to claim 13, wherein the species of organism is selected from animal species, bacterial species, fungal species, and plant species.

15. The method according to claim 13, wherein the isolated nucleic acid is a mixture of nucleic acid from a minor species of organism and a dominant species of organism, and wherein the inverted repeat region of the primer is an inverted repeat of a non-conserved internal region of an amplicon of nucleic acid of the dominant species of organism.

16. The method according to claim 13, wherein the nucleic acid is DNA.

17. The method according to claim 16, wherein the DNA is part of the genes encoding ribosomal RNAs.

18. The method according to claim 13, wherein the species of organism is a bacterial species.

19. The method according to claim 17, wherein the inverted repeat region of the forward primer is an inverted repeat of a region within the amplicon of the 16S ribosomal DNA of a pre-selected species of organism.

20. The method according to claim 1, wherein the target and non-target nucleic acids are allelic variants of a gene or different members of a gene family.

21. The method according to claim 1, wherein the target nucleic acid or the at least one non-target nucleic acid contains methylated nucleic acid.

22. The method according to claim 21, wherein selective amplification of methylated nucleic acid is performed.

23. The method according to claim 1, wherein the target nucleic acid or the at least one non-target nucleic acid is subjected to a modification step prior to the amplification.

24. The method according to claim 23, wherein the at least one non-target nucleic acid is modified during the modification step.

25. The method according to claim 23, wherein the modification step is a chemical modification.

26. The method according to claim 25, wherein the modification step converts unmethylated cytosines to another nucleotide capable of forming a base pair with adenine while methylated cytosines are unchanged or are converted to a nucleotide capable of forming a base pair with guanine.

27. The method according to claim 26, wherein the modification step converts unmethylated cytosines to uracil.

28. The method according to claim 25, wherein the chemical modification step is a bisulphite treatment.

29. The method according to claim 21, wherein the inverted repeat region of the forward primer comprises a sufficient number of nucleotides to allow annealing and extension on a matched sequence of the methylated non-target nucleic acid and sufficient mismatches not to allow annealing and/or extension of unmethylated target nucleic acid.

30. An assay for abnormal methylation of cytosine at a site or sites within the glutathione-S-transferase (GST) Pi gene and/or its regulatory flanking sequences, wherein the assay comprises exposing isolated DNA to reactants and conditions for the amplification of a target region within the GST Pi gene and/or its regulatory flanking sequences, the target region being one or more sites at which abnormal cytosine methylation occurs, the amplification being carried out using forward and reverse oligonucleotide primers, the forward primer comprising:

a primer region that can prime and extend on both the target region that is methylated and a non-target region that is non-methylated, within the isolated DNA; and a region that is an inverted repeat of an internal sequence of an amplicon of the non-target region but which contains at least one mismatch to the corresponding internal sequence of the target nucleic region, the inverted repeat region being 5' of the primer region;

wherein during amplification the forward primer extends on the target and non-target regions to give rise to first strand products and the reverse primer extends on the first strand products to give rise to second strand products; and wherein the inverted repeat region located 5' of the primer region of the forward primer is copied during second strand synthesis to form a 3' terminal sequence within the second strand products; and wherein the 3' terminal sequence of the second strand product corresponding to the non target region anneals to an upstream region of the same product corresponding to the internal sequence of the amplicon and is extended to form a hairpin loop structure that inhibits further amplification of the non-target region; and determining the presence of amplified DNA.

31. The assay according to claim 30, wherein the target region is within the region of the GST-Pi gene and/or its regulatory flanking sequences defined by CpG sites −43 to +55.

32. The assay according to claim 30, wherein the isolated DNA is subjected to chemical modification to convert unmethylated cytosines to uracil prior to amplification.

33. The assay according to claim 32, wherein the chemical modification is achieved by bisulphite treatment.

34. The assay according to claim 30, wherein the abnormal methylation of cytosine at a site or sites within the glutathione-S-transferase (GST) Pi gene and/or its regulatory flanking sequences is associated with a disease or condition in a subject.

35. The assay according to claim 34, wherein the disease or condition is a cancer.

36. The assay according to claim 35, wherein the cancer is prostate, liver, or breast cancer.

* * * * *

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: Primer NR-R1i
<220> FEATURE:
<221> NAME/KEY: misc_feature
<222> LOCATION: (7)..(7)
<223> OTHER INFORMATION: n is Inosine
<220> FEATURE:
<221> NAME/KEY: misc_feature
<222> LOCATION: (12)..(13)
<223> OTHER INFORMATION: n is Inosine

<400> SEQUENCE: 1
gagctgncga cnnccatgca                                          20

<210> SEQ ID NO 2
<211> LENGTH: 21
<212> TYPE: DNA
<213> ORGANISM: Artificial Sequence
<220> FEATURE:
<223> OTHER INFORMATION: Primer NR-F1i
<220> FEATURE:
<221> NAME/KEY: misc_feature
<222> LOCATION: (8)..(9)
<223> OTHER INFORMATION: n is Inosine
<220> FEATURE:
<221> NAME/KEY: misc_feature
<222> LOCATION: (12)..(13)
<223> OTHER INFORMATION: n is Inosine

<400> SEQUENCE: 2
gtagtccnng cnntaaacga t                                        21

<210> SEQ ID NO 3
<211> LENGTH: 39
<212> TYPE: DNA
<213> ORGANISM: Artificial Sequence
<220> FEATURE:
<223> OTHER INFORMATION: Primer EHL48
<220> FEATURE:
<221> NAME/KEY: misc_feature
<222> LOCATION: (26)..(27)
<223> OTHER INFORMATION: n is Inosine
<220> FEATURE:
<221> NAME/KEY: misc_feature
```

```
<222> LOCATION: (30)..(31)
<223> OTHER INFORMATION: n is Inosine

<400> SEQUENCE: 3
gacttaacgc gttagctcgt agtccnngcn ntaaacgat                              39

<210> SEQ ID NO 4
<211> LENGTH: 43
<212> TYPE: DNA
<213> ORGANISM: Artificial Sequence
<220> FEATURE:
<223> OTHER INFORMATION: Primer EHL 64
<220> FEATURE:
<221> NAME/KEY: misc_feature
<222> LOCATION: (30)..(31)
<223> OTHER INFORMATION: n is Inosine
<220> FEATURE:
<221> NAME/KEY: misc_feature
<222> LOCATION: (34)..(35)
<223> OTHER INFORMATION: n is Inosine

<400> SEQUENCE: 4
gacttaacgc gttagctccg gagtagtccn ngcnntaaac gat                        43

<210> SEQ ID NO 5
<211> LENGTH: 40
<212> TYPE: DNA
<213> ORGANISM: Artificial Sequence
<220> FEATURE:
<223> OTHER INFORMATION: Primer EHL 2a
<220> FEATURE:
<221> NAME/KEY: misc_feature
<222> LOCATION: (27)..(28)
<223> OTHER INFORMATION: n is a, c, g or t
<220> FEATURE:
<221> NAME/KEY: misc_feature
<222> LOCATION: (31)..(32)
<223> OTHER INFORMATION: n is Inosine

<400> SEQUENCE: 5
acaacctcca agtcgacatg tagtccnngc nntaaacgat                            40

<210> SEQ ID NO 6
<211> LENGTH: 38
<212> TYPE: DNA
<213> ORGANISM: Artificial Sequence
<220> FEATURE:
<223> OTHER INFORMATION: Primer SAHL
<220> FEATURE:
<221> NAME/KEY: misc_feature
<222> LOCATION: (25)..(26)
<223> OTHER INFORMATION: n is Inosine
<220> FEATURE:
<221> NAME/KEY: misc_feature
<222> LOCATION: (29)..(30)
<223> OTHER INFORMATION: n is Inosine

<400> SEQUENCE: 6
cgacacctcg tatccatgta gtccnngcnn taaacgat                              38

<210> SEQ ID NO 7
<211> LENGTH: 397
<212> TYPE: DNA
<213> ORGANISM: Human methylated GST fragment

<400> SEQUENCE: 7
cgggatcgta gcggttttag ggaattttttt tcgcgatgt tcggcgcgt tagttcgttg       60 cgtatatttc gttgcggttt ttttttttgtt gtttgtttat ttttaggtt tcgttgggga    120
```

```
tttgggaaag agggaaaggt tttttcggtt agttgcgcgg cgatttcggg gattttaggg      180 cgttttttg cggtcgacgt tcggggtgta gcggtcgtcg gggttggggt cggcgggagt       240
tcgcgggatt ttttagaaga gcggtcggcg tcgtgattta gtattggggc ggagcggggc      300
gggattattt ttataaggtt cggaggtcgc ggagttttcg ttggagtttc gtcgtcgtag      360
ttttcgttat tagtgagtac gcgcggttcg cgttttc                               397
```

```
<210> SEQ ID NO 8
<211> LENGTH: 120
<212> TYPE: DNA
<213> ORGANISM: Human unmethylated GST fragment

<400> SEQUENCE: 8
tggttttagg gaattttttt ttgtgatgtt ttggtgtgtt agtttgttgt gtatattttg       60
ttgtggtttt ttttttgttg tttgtttatt tttaggtttt tgttggggat ttgggaaaga     120
```

```
<210> SEQ ID NO 9
<211> LENGTH: 20
<212> TYPE: DNA
<213> ORGANISM: Artificial Sequence
<220> FEATURE:
<223> OTHER INFORMATION: Primer F2

<400> SEQUENCE: 9
ggttttaggg aattttttt                                                    20
```

```
<210> SEQ ID NO 10
<211> LENGTH: 20
<212> TYPE: DNA
<213> ORGANISM: Artificial Sequence
<220> FEATURE:
<223> OTHER INFORMATION: Primer R1T

<400> SEQUENCE: 10 caccttttccc aaatccccaa                                                  20
```

```
<210> SEQ ID NO 11
<211> LENGTH: 39
<212> TYPE: DNA
<213> ORGANISM: Artificial Sequence
<220> FEATURE:
<223> OTHER INFORMATION: Primer LUH F2

<400> SEQUENCE: 11
acaccaaaac atcacaaaag gttttaggga attttttt                               39
```

```
<210> SEQ ID NO 12
<211> LENGTH: 40
<212> TYPE: DNA
<213> ORGANISM: Artificial Sequence
<220> FEATURE:
<223> OTHER INFORMATION: Primer CLUH F2

<400> SEQUENCE: 12
cacaccaaaa catcacaaaa ggttttaggg aattttttt                              40
```

```
<210> SEQ ID NO 13
<211> LENGTH: 40
<212> TYPE: DNA
<213> ORGANISM: Artificial Sequence
<220> FEATURE:
<223> OTHER INFORMATION: Primer CLUR F2

<400> SEQUENCE: 13
```

-continued

```
ccatcaacaa aaaacacaca ggttttaggg aattttttt                           40

<210> SEQ ID NO 14
<211> LENGTH: 42
<212> TYPE: DNA
<213> ORGANISM: Artificial Sequence
<220> FEATURE:
<223> OTHER INFORMATION: Primer FT F2

<400> SEQUENCE: 14
aacacaccaa aacatcacaa aaggttttag ggaattttt tt                        42

<210> SEQ ID NO 15
<211> LENGTH: 19
<212> TYPE: DNA
<213> ORGANISM: Artificial Sequence
<220> FEATURE:
<223> OTHER INFORMATION: Inverse repeat

<400> SEQUENCE: 15
acaccaaaac atcacaaaa                                                 19

<210> SEQ ID NO 16
<211> LENGTH: 19
<212> TYPE: DNA
<213> ORGANISM: Human

<400> SEQUENCE: 16
ttttgtgatg ttttggtgt                                                 19

<210> SEQ ID NO 17
<211> LENGTH: 29
<212> TYPE: DNA
<213> ORGANISM: Artificial Sequence
<220> FEATURE:
<223> OTHER INFORMATION: Probe PRB M

<400> SEQUENCE: 17
ttgcgtatat ttcgttgcgg ttttttttt                                      29

<210> SEQ ID NO 18
<211> LENGTH: 34
<212> TYPE: DNA
<213> ORGANISM: Artificial Sequence
<220> FEATURE:
<223> OTHER INFORMATION: Probe PRB U

<400> SEQUENCE: 18
ttgtgtatat tttgttgtgg tttttttttt gttg                                34

<210> SEQ ID NO 19
<211> LENGTH: 26
<212> TYPE: DNA
<213> ORGANISM: Artificial Sequence
<220> FEATURE:
<223> OTHER INFORMATION: Primer GSATA56

<400> SEQUENCE: 19
gttttgtgaa gagggtgtgt aagttt                                         26

<210> SEQ ID NO 20
<211> LENGTH: 23
<212> TYPE: DNA
<213> ORGANISM: Artificial Sequence
<220> FEATURE:
```

```
<223> OTHER INFORMATION: Primer R4

<400> SEQUENCE: 20
aaaacctttc cctctttccc aaa                                              23

<210> SEQ ID NO 21
<211> LENGTH: 27
<212> TYPE: DNA
<213> ORGANISM: Artificial Sequence
<220> FEATURE:
<223> OTHER INFORMATION: Primer F52A

<400> SEQUENCE: 21
gggattattt ttataaggtt aggaggt                                          27

<210> SEQ ID NO 22
<211> LENGTH: 26
<212> TYPE: DNA
<213> ORGANISM: Artificial Sequence
<220> FEATURE:
<223> OTHER INFORMATION: Primer GSTintR1

<400> SEQUENCE: 22
cccatactaa aaactctaaa ccccat                                           26

<210> SEQ ID NO 23
<211> LENGTH: 45
<212> TYPE: DNA
<213> ORGANISM: Artificial Sequence
<220> FEATURE:
<223> OTHER INFORMATION: Primer HLint5-10

<400> SEQUENCE: 23
tgtgtggttt gtgttttgc ccatactaaa aactctaaac cccat                       45

<210> SEQ ID NO 24
<211> LENGTH: 51
<212> TYPE: DNA
<213> ORGANISM: Artificial Sequence
<220> FEATURE:
<223> OTHER INFORMATION: Primer HLint5-10X

<400> SEQUENCE: 24
tgtgtggttt gtgtttttgg ggatgcccat actaaaaact ctaaaccccca t              51

<210> SEQ ID NO 25
<211> LENGTH: 21
<212> TYPE: DNA
<213> ORGANISM: Artificial Sequence
<220> FEATURE:
<223> OTHER INFORMATION: Primer GSTintR11i
<220> FEATURE:
<221> NAME/KEY: misc_feature
<222> LOCATION: (18)..(18)
<223> OTHER INFORMATION: n is Inosine

<400> SEQUENCE: 25
ctctaaaccc catccccnaa a                                                21

<210> SEQ ID NO 26
<211> LENGTH: 40
<212> TYPE: DNA
<213> ORGANISM: Artificial Sequence
<220> FEATURE:
<223> OTHER INFORMATION: Primer HLint5-10Ni
<220> FEATURE:
<221> NAME/KEY: misc_feature
```

```
<222> LOCATION: (37)..(37)
<223> OTHER INFORMATION: n = Inosine

<400> SEQUENCE: 26
tgtgtggttt gtgttttttgc tctaaacccc atccccnaaa                          40

<210> SEQ ID NO 27
<211> LENGTH: 279
<212> TYPE: DNA
<213> ORGANISM: E. coli

<400> SEQUENCE: 27
tcgtagtcca cgccgtaaac gatgtcgact tggaggttgt gcccttgagg cgtggcttcc     60
ggagctaacg cgttaagtcg accgcctggg gagtacggcc gcaaggttaa aactcaaatg    120
aattgcgggg gcccgcacaa gcggtggagc atgtggttta attcgatgca acgcgaagaa    180
ccttacctgg tcttgacatc cacggaagtt ttcagagatg agaatgtgcc ttcgggaacc    240
gtgagacagg tgctgcatgg ctgtcgtcag ctcgtgttg                           279

<210> SEQ ID NO 28
<211> LENGTH: 280
<212> TYPE: DNA
<213> ORGANISM: Sulfobacillus acidophilus

<400> SEQUENCE: 28
cggtagtcca cgccgtaaac gatggatacg aggtgtcgcg ggggtccacc tcgcggtgcc     60
ggagctaacg cactcagtat cccgcctggg gagtacggcc gcaaggttga aactcaaagg    120
aattgcgggg gcccgcacaa gcagtggagc atgtggttta attcgacgca acgcgcagaa    180
ccttaccagg gctagacggg accgtgagcc gcgcgaaagc gcggggctgc ttcggcagag    240
cggtcgtcag gtgctgcatg gttgtcgtca gctcgtgtcg                         280

<210> SEQ ID NO 29
<211> LENGTH: 274
<212> TYPE: DNA
<213> ORGANISM: Sulfobacillus thermosulfidooxidans

<400> SEQUENCE: 29
cggtagtcca cgccgtaaac gatgactagg tgtccgccgg gtccaccggg cggtgccgga     60
gctaacgcac taagtacccc gcctggggag tacgccgca aggttgaaac tcaaaggaat    120
tgcgggggcc cgcacaagcc gtggagcatg tggtttaatt cgacgcaacg cggagaacct    180
taccaggact ggacacgctc gtgagcgccg cgaaagcggc gggccctccg gggagcgagc    240
gcaggtgctg catggctgtc gtcagctcgt gtcg                               274

<210> SEQ ID NO 30
<211> LENGTH: 169
<212> TYPE: DNA
<213> ORGANISM: Human GSTP1 Intragenic Region

<400> SEQUENCE: 30
cagcactggg gcggagcggg gcgggaccac ccttataagg ctcggaggcc gcgaggcctt     60
cgctggagtt tcgccgccgc agtcttcgcc accagtgagt acgcgcgcc cgcgtccccg    120 tcagagctcc gggatggggc cagcatgggg tgtgtggttt gtgttttg                169

<210> SEQ ID NO 31
<211> LENGTH: 175
<212> TYPE: DNA
```

-continued

```
<213> ORGANISM: Human GSTP1 Intragenic Region

<400> SEQUENCE: 31
tagtattggg gcggagcggg gcgggattat ttttataagg ttcggaggtc gcgaggtttt      60
cgttggagtt tcgtcgtcgt agttttcgtt attagtgagt acgcgcggtt tgtgttttg      120 gggatggggt ttagagtttt tagtatgggg tgtgtggttt gtgttttggg ggatg          175

<210> SEQ ID NO 32
<211> LENGTH: 27
<212> TYPE: DNA
<213> ORGANISM: Artificial Sequence
<220> FEATURE:
<223> OTHER INFORMATION: Primer GSTP1 F52A

<400> SEQUENCE: 32
gggattattt ttataaggtt aggaggt                                          27

<210> SEQ ID NO 33
<211> LENGTH: 21
<212> TYPE: DNA
<213> ORGANISM: Artificial Sequence
<220> FEATURE:
<223> OTHER INFORMATION: Primer GSTIntR11i
<220> FEATURE:
<221> NAME/KEY: misc_feature
<222> LOCATION: (4)..(4)
<223> OTHER INFORMATION: n is Inosine

<400> SEQUENCE: 33
aaanccccat ccccaaatct c                                                21

<210> SEQ ID NO 34
<211> LENGTH: 26
<212> TYPE: DNA
<213> ORGANISM: Artificial Sequence
<220> FEATURE:
<223> OTHER INFORMATION: Primer GSTintR1

<400> SEQUENCE: 34
taccccaaat ctcaaaaatc ataccc                                           26

<210> SEQ ID NO 35
<211> LENGTH: 21
<212> TYPE: DNA
<213> ORGANISM: Artificial Sequence
<220> FEATURE:
<223> OTHER INFORMATION: EHL48 Primer

<400> SEQUENCE: 35
atcgtttagg gcggggacta c                                                21

<210> SEQ ID NO 36
<211> LENGTH: 18
<212> TYPE: DNA
<213> ORGANISM: Artificial Sequence
<220> FEATURE:
<223> OTHER INFORMATION: EHL48 Head

<400> SEQUENCE: 36
gagctaacgc gttaagtc                                                    18

<210> SEQ ID NO 37
<211> LENGTH: 24
<212> TYPE: DNA
<213> ORGANISM: Artificial Sequence
```

```
<220> FEATURE:
<223> OTHER INFORMATION: EHL48 Head

<400> SEQUENCE: 37
aggcctcgat tgcgcaattc agct                                              24

<210> SEQ ID NO 38
<211> LENGTH: 24
<212> TYPE: DNA
<213> ORGANISM: Artificial Sequence
<220> FEATURE:
<223> OTHER INFORMATION: EHL48 Head

<400> SEQUENCE: 38
aggcctcgat tgcgtgagtc atct                                              24

<210> SEQ ID NO 39
<211> LENGTH: 61
<212> TYPE: DNA
<213> ORGANISM: Artificial Sequence
<220> FEATURE:
<223> OTHER INFORMATION: LUH-F2 Primer

<400> SEQUENCE: 39
actaacacac caaaacatca caaaaaaaaa ttccctaaaa cctttttgtga tgttttggtg      60 t                                                                       61

<210> SEQ ID NO 40
<211> LENGTH: 19
<212> TYPE: DNA
<213> ORGANISM: Artificial Sequence
<220> FEATURE:
<223> OTHER INFORMATION: LUHF2 Head Primer

<400> SEQUENCE: 40
aaaacactac aaaaccaca                                                    19

<210> SEQ ID NO 41
<211> LENGTH: 20
<212> TYPE: DNA
<213> ORGANISM: Artificial Sequence
<220> FEATURE:
<223> OTHER INFORMATION: CLUHF2 Head Primer

<400> SEQUENCE: 41
aaaacactac aaaaccacac                                                   20

<210> SEQ ID NO 42
<211> LENGTH: 22
<212> TYPE: DNA
<213> ORGANISM: Artificial Sequence
<220> FEATURE:
<223> OTHER INFORMATION: FTF2 Head Primer

<400> SEQUENCE: 42
aaaacactac aaaaccacac aa                                                22
```